United States Patent
Lamas-Peteira et al.

(10) Patent No.: US 8,778,946 B2
(45) Date of Patent: Jul. 15, 2014

(54) 3-SUBSTITUTED-6-(PYRIDINYLMETHOXY)-PYRROLOPYRIDINE COMPOUNDS

(75) Inventors: Carlos Lamas-Peteira, Madrid (ES);
Simon James Richards, Surrey (GB);
Selma Sapmaz, Hampshire (GB);
Magnus Wilhelm Walter, Richmond (GB)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/882,765

(22) PCT Filed: Nov. 17, 2011

(86) PCT No.: PCT/US2011/061212
§ 371 (c)(1),
(2), (4) Date: May 1, 2013

(87) PCT Pub. No.: WO2012/074769
PCT Pub. Date: Jun. 7, 2012

(65) Prior Publication Data
US 2013/0225602 A1    Aug. 29, 2013

Related U.S. Application Data

(60) Provisional application No. 61/439,438, filed on Feb. 4, 2011.

(30) Foreign Application Priority Data

Dec. 2, 2010   (EP) .................................... 103823258

(51) Int. Cl.
*C07D 471/04* (2006.01)
*A61K 31/496* (2006.01)
*C07D 487/04* (2006.01)

(52) U.S. Cl.
CPC ............ *C07D 487/04* (2013.01); *C07D 471/04* (2013.01)
USPC ...................... 514/253.04; 544/362

(58) Field of Classification Search
None
See application file for complete search history.

(56) References Cited

U.S. PATENT DOCUMENTS

2009/0197881 A1    8/2009 Kugimiya et al.

FOREIGN PATENT DOCUMENTS

| WO | 2005/056012 A1 | 6/2005 |
|----|----------------|--------|
| WO | 2005/056524 A2 | 6/2005 |
| WO | 2005/085248 A1 | 9/2005 |
| WO | 2010/002820 A1 | 1/2010 |
| WO | 2010/124047 A1 | 10/2010 |

OTHER PUBLICATIONS

Buttelmann, et al., Arylmethoxypyridines as novel, potent and orally active mGlu5 receptor antagonists, Bioorganic & Medicinal Chemistry Letters 16 (2006) 1892-1897.

Slassi et al., Recent Advances in Non-Competitive mGlu5 Receptor Antagonists and their Potential Therapeutic Applications, Current Topics in Medicinal Chemistry, 2005, 5, 897-911.

*Primary Examiner* — Emily Bernhardt
(74) *Attorney, Agent, or Firm* — Mark A. Winter

(57) ABSTRACT

The invention provides certain 3-substituted-6-(pyridinylmethoxy)-pyrrolopyridine compounds, particularly compounds of formula I and pharmaceutical compositions thereof. The invention further provides methods of using a compound of formula I to treat Parkinsons disease Formula (I).

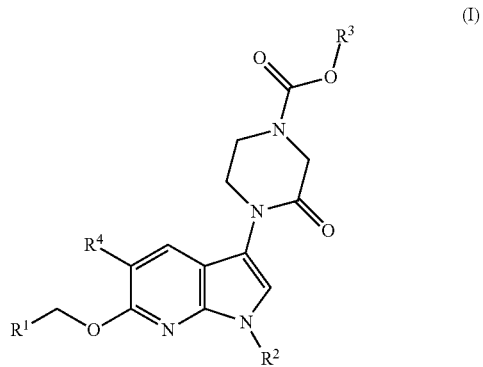

9 Claims, No Drawings

3-SUBSTITUTED-6-(PYRIDINYLMETHOXY)-PYRROLOPYRIDINE COMPOUNDS

The invention provides certain 3-substituted-6-(pyridinylmethoxy)-pyrrolopyridine compounds, particularly certain 3-oxopiperazinyl-6-(pyridinylmethoxy)-pyrrolopyridine compounds, pharmaceutical compositions thereof, methods of using the same, and processes for preparing the same.

L-Glutamate is the major excitatory neurotransmitter in the central nervous system and is referred to as an excitatory amino acid. Glutamate receptors are composed of two major subtypes: the ligand-gated ion-channel ionotropic receptors, and the G-protein-coupled seven-transmembrane-domain metabotropic receptors (mGluRs). The metabotropic family comprises eight members and is sub-divided into three groups based on sequence similarity, signal transduction, and pharmacology. Group I receptors (mGluR$_1$ and mGluR$_5$, and their splice variants) are positively coupled to inositol phosphate hydrolysis and the generation of an intracellular calcium signal. Group II receptors (mGluR$_2$ and mGluR$_3$) and Group III receptors (mGluR$_4$, mGluR$_6$, mGluR$_7$, and mGluR$_8$) are negatively coupled to adenylyl cyclase and regulate cyclic AMP levels by indirectly inhibiting adenylyl cyclase activity. The mGlu receptor subtypes have unique expression patterns in the central nervous system, which can be targeted with new and selective agents. See, for example, Slassi, A. et. al., Current Topics in Medicinal Chemistry (2005), 5, 897-911, in which mGluR$_5$ antagonists are described as useful as antiparkinsonian agents in animal models of Parkinson's disease. In addition, mGluR$_5$ antagonists are believed to be useful in models of anxiety, fragile X syndrome, substance dependence and withdrawal including alcohol self-administration, as well as models of inflammatory and neuropathic pain.

United States Patent Application Publication US 2009/0197881 discloses certain azaindole derivative compounds as antagonists of the prostaglandin receptor DP, and further discloses the compounds as useful in treating allergic diseases including asthma.

The compounds of the present invention are selective antagonists of the Group I metabotropic receptors, particularly the mGluR$_5$ receptor (mGluR$_5$), especially with respect to selectivity over mGluR$_2$, mGluR$_3$ and mGluR$_4$. Surprisingly, within the Group I metabotrobic receptors, compounds of the present invention are selective for mGluR$_5$ with respect to mGluR$_1$. The compounds of the present invention are believed to be useful for the treatment of conditions associated with mGluR$_5$ receptors, such as Parkinson's disease, pain, substance dependence and withdrawal, anxiety including generalized anxiety disorder, depression including major depressive disorders, as well as anxiety co-morbid with depression (mixed anxiety depression disorder) including generalized anxiety disorder co-morbid with major depressive disorder.

The present invention provides new compounds that are antagonists of mGluR$_5$ and, as such, are believed to be useful in treatment of the disorders discussed above. Such new compounds could address the need for safe and effective treatments of conditions associated with the above receptors without attending side effects.

The present invention provides a compound of formula I, or a pharmaceutically acceptable salt thereof,

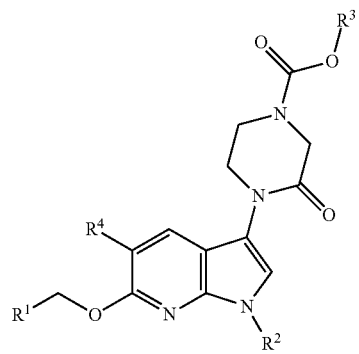

wherein
R$^1$ is pyridinyl optionally substituted with one group selected from fluoro, methyl or methoxy;
R$^2$ is C$_1$-C$_3$ alkyl or cyclopropyl;
R$^3$ is C$_1$-C$_3$ alkyl, 2-fluoroethyl, 2-methoxyethyl, or cyclobutyl; and
R$^4$ is hydrogen, fluoro, chloro or methyl.

Further, the present invention provides a pharmaceutical composition comprising a compound of formula I, or a pharmaceutically acceptable salt thereof, and a pharmaceutically acceptable carrier, diluent or excipient. In a particular embodiment, the composition further comprises one or more other therapeutic agents.

Further, the present invention provides a compound of formula I, or a pharmaceutically acceptable salt thereof, for use in therapy.

Further, the present invention provides a compound of formula I, or a pharmaceutically acceptable salt thereof, for use in the treatment of Parkinson's disease.

Further, the present invention provides the use of a compound of formula I, or a pharmaceutically acceptable salt thereof, for the manufacture of a medicament for treating Parkinson's disease.

Further, the present invention provides the use of a compound of formula I, or a pharmaceutically acceptable salt thereof, for the manufacture of a medicament for treating depression.

Further, the present invention provides a method of treating Parkinson's disease, comprising administering to a patient in need thereof an effective amount of a compound of formula I, or a pharmaceutically acceptable salt thereof.

The term "C$_1$-C$_3$ alkyl" refers to a straight or branched alkyl chain having from one to three carbon atoms and includes methyl, ethyl, n-propyl and i-propyl.

A particular compound of formula I or a pharmaceutically acceptable salt thereof is one wherein,
R$^1$ is 2-pyridinyl, 3-pyridinyl, 4-pyridinyl, 5-fluoro-2-pyridinyl, 5-methyl-2-pyridinyl, 5-methoxy-2-pyridinyl, 3-methyl-2-pyridinyl or 6-methyl-2-pyridinyl;
R$^2$ is methyl, ethyl or cyclopropyl;
R$^3$ is methyl, ethyl, n-propyl, i-propyl, 2-fluoroethyl, 2-methoxyethyl, or cyclobutyl; and
R$^4$ is hydrogen, fluoro, chloro or methyl.

A particular compound of formula I or a pharmaceutically acceptable salt thereof is one wherein R$^1$ is 2-pyridinyl, 3-pyridinyl, 4-pyridinyl, 5-fluoro-2-pyridinyl, 5-methyl-2-pyridinyl, 5-methoxy-2-pyridinyl, 3-methyl-2-pyridinyl or 6-methyl-2-pyridinyl.

A particular compound of formula I or a pharmaceutically acceptable salt thereof is one wherein R$^2$ is methyl, ethyl or cyclopropyl.

A particular compound of formula I or a pharmaceutically acceptable salt thereof is one wherein R³ is methyl, ethyl, n-propyl, i-propyl, 2-fluoroethyl, 2-methoxyethyl, or cyclobutyl.

A particular compound of formula I or a pharmaceutically acceptable salt thereof is one wherein R⁴ is hydrogen, fluoro, chloro or methyl.

A particular compound of formula I or a pharmaceutically acceptable salt thereof is one wherein R¹ is 2-pyridinyl.

A particular compound of formula I or a pharmaceutically acceptable salt thereof is one wherein R² is methyl.

A particular compound of formula I or a pharmaceutically acceptable salt thereof is one wherein R³ is ethyl.

A particular compound of formula I or a pharmaceutically acceptable salt thereof is one wherein R⁴ is hydrogen.

A particular compound of formula I is ethyl 4-[1-methyl-6-(pyridin-2-ylmethoxy)-1H-pyrrolo[2,3-b]pyridin-3-yl]-3-oxopiperazine-1-carboxylate or a pharmaceutically acceptable salt thereof.

A further embodiment of the present invention include a process for preparing a compound of formula I, or a pharmaceutically acceptable salt thereof, comprising A) reacting a compound of formula II where X¹ is a halo group

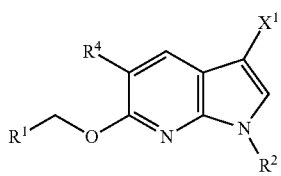

II with an R³-3-oxopiperazine-1-carboxylate of formula:

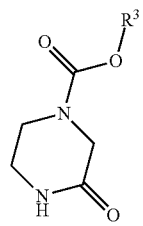

or alternatively

B) acylating a compound of formula III;

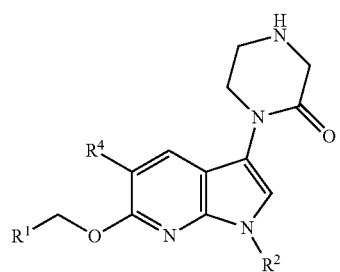

III with a R³ carbonohalogen of formula:

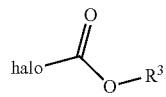

where after, when a pharmaceutically acceptable salt of the compound of formula I is required, it is obtained by reacting a basic compound of formula I with a physiologically acceptable acid or by any other conventional procedure.

It is understood that compounds of the present invention may exist as stereoisomers. While all enantiomers, diastereomers, and mixtures thereof, are contemplated within the present invention, preferred embodiments are single diastereomers, and more preferred embodiments are single enantiomers.

It is understood that compounds of the present invention may exist as tautomeric forms. When tautomeric forms exist, each form and mixtures thereof, are contemplated in the present invention.

The term "pharmaceutically acceptable salt" includes acid addition salt that exists in conjunction with the basic portion of a compound of formula I. Such salts include the pharmaceutically acceptable salts listed in Handbook of Pharmaceutical Salts: Properties, Selection and Use, P. H. Stahl and C. G. Wermuth (Eds.), Wiley-VCH, New York, 2002 which are known to the skilled artisan.

In addition to pharmaceutically acceptable salts, other salts are included in the invention. They may serve as intermediates in the purification of compounds or in the preparation of other pharmaceutically-acceptable salts, or are useful for identification, characterization or purification.

A compound of the invention is expected to be useful whenever antagonism of the mGluR₅ receptor is indicated. A further embodiment, a compound of the invention is expected to be useful for the treatment of Parkinson's disease and disorders associated with Parkinson's disease. In particular, a compound of the invention is expected to be useful for the treatment of dyskinesia including Parkinson's disease levodopa (L-dopa) induced dyskinesia (PD-LID).

As used herein, the term "patient" refers to a warm blooded animal such as a mammal and includes a human. A human is a preferred patient.

It is also recognized that one skilled in the art may affect Parkinson's disease by treating a patient presently displaying symptoms with an effective amount of the compound of formula I. Thus, the terms "treatment" and "treating" are intended to refer to all processes wherein there may be a slowing, interrupting, arresting, controlling, or stopping of the progression of an existing disorder and/or symptoms thereof, but does not necessarily indicate a total elimination of all symptoms.

It is also recognized that one skilled in the art may affect Parkinson's disease by treating a patient at risk of future symptoms with an effective amount of the compound of formula I and is intended to include prophylactic treatment of such.

As used herein, the term "effective amount" of a compound of formula I refers to an amount, that is, the dosage which is effective in treating the disorder, such as Parkinson's disease described herein. The attending diagnostician, as one skilled in the art, can readily determine an effective amount by the use of conventional techniques and by observing results obtained under analogous circumstances. In determining an effective amount, the dose of a compound of formula I, a number of factors are considered by the attending diagnostician, including, but not limited to the compound of formula I to be administered; the co-administration of other agents, if used; the species of mammal; its size, age, and general health; the degree of involvement or the severity of the disorder, such as Parkinson's disease; the response of the individual patient; the mode of administration; the bioavailability characteristics of the preparation administered; the dose regimen selected; the use of other concomitant medication; and other relevant circumstances.

A compound of formula I may be used in combination with other drugs that are used in the treatment/prevention/suppression or amelioration of the diseases or conditions for which compounds of formula I are useful including Parkinson's disease. Such other drug(s) may be administered, by a route and in an amount commonly used therefore, contemporaneously or sequentially with a compound of formula I. When a compound of formula I is used contemporaneously with one or more other drugs, a pharmaceutical unit dosage form containing such other drugs in addition to the compound of formula I is preferred. Accordingly, the pharmaceutical compositions of the present invention include those that also contain one or more other active ingredients, in addition to a compound of formula I. Examples of other active ingredients effective in the treatment of Parkinson's disease that may be combined with a compound of formula I, either administered separately or in the same pharmaceutical include, but are not limited to:

(a) dopamine precursors such as levodopa; melevodopa, and etilevodopa;

(b) dopamine agonists including pramipexole, ropinorole, apomorphine, rotigotine, bromocriptine, cabergoline, and pergolide;

(c) monamine oxidase B (MAO B) inhibitors such as selegiline and rasagiline;

(d) catechol O-methyltransferase (COMT) inhibitors such as tolcapone and entacapone;

(e) anticholinergic agents including benztropine, trihexyphenidyl, procyclidine, and biperiden;

(f) glutamate (NMDA) blocking drugs such as amantadine;

(g) adenosine A2a antagonists such as istradefylline and preladenant;

(h) 5-HT1a antagonists such as piclozotan and pardoprunox; or (i) alpha 2 antagonists such as atipamezole and fipamezole.

The compounds of the present invention can be administered alone or in the form of a pharmaceutical composition, that is, combined with pharmaceutically acceptable carriers or excipients, the proportion and nature of which are determined by the solubility and chemical properties, including stability, of the compound selected, the chosen route of administration, and standard pharmaceutical practice. The compounds of the present invention, while effective themselves, may be formulated and administered in the form of their pharmaceutically acceptable salts, for convenience of crystallization, increased solubility, and the like.

Thus, the present invention provides pharmaceutical compositions comprising a compound of the formula I and a pharmaceutically acceptable carrier, diluent or excipient.

One skilled in the art of preparing formulations can readily select the proper form and mode of administration depending upon the particular characteristics of the compound selected, the disorder or condition to be treated, the stage of the disorder or condition, and other relevant circumstances (See, e.g., Remington: The Science and Practice of Pharmacy, D. B. Troy, Editor, 21st Edition., Lippincott, Williams & Wilkins, 2006).

Human $mGluR_5$ and $mGluR_1$ in Vitro Functional Assays

The activation of G-protein coupled receptors (GPCRs) that are coupled to Gq proteins results in a change in intracellular calcium concentration. This functional response can be measured in a kinetic assay using calcium-sensitive dyes and a fluorescent imaging plate reader using a standard technique known as FLIPR (MDS Analytical Technologies, Sunnyvale, Calif.).

Stable cell line preparation and assay techniques are adapted from Kingston, A. E., et. al. (1995) Neuropharmacology 34: 887-894. Briefly, clonal cell lines expressing recombinant human mGlu5a and mGlu1α receptors are transfected into AV-12 cells (American Type Culture Collection, Manassas, Va.) containing the rat EAAT1 glutamate transporter. Cells are grown in Dulbecco's Modified Eagle's Medium (DMEM; Invitrogen, Carlsbad, Calif.) supplemented with 5% fetal bovine serum, 1 mM L-glutamine, 1 mM sodium pyruvate, 10 mM HEPES (4-(2-hydroxyethyl)-1-piperazineethanesulfonic acid), 0.75 mg/ml geneticin, and 0.3 mg/ml hygromycin B at 37° C. in an incubator with 95% relative humidity and 5% $CO_2$. Confluent cultures are passaged biweekly.

For the functional assays, cells are seeded in growth medium lacking selection antibiotics at a density of 65K per well into 96-well, black/clear bottom, poly-D-lysine coated microplates and incubated for 18-20 hours prior to the experiment. After removing the medium, cells are dye-loaded with 8 μM Fluo-3 (Invitrogen) in assay buffer consisting of Hanks Balanced Salt Solution (Invitrogen) supplemented with 20 mM HEPES for 1.5 h at 25° C. Compounds are serially diluted into DMSO and then diluted once into assay buffer; the final DMSO concentration in the assay is 0.625%. A single-addition FLIPR assay generating an 11-point dose response curve for the agonist glutamate is conducted prior to each experiment to estimate the amount of agonist needed to induce an $EC_{90}$ response. The antagonist effects of compounds are quantified in the FLIPR instrument in 10-point dose curves by comparing the peak fluorescent responses to the agonist glutamate in the presence and absence of compound. Specifically, the compound effect is measured as maximal minus minimal peak heights in relative fluorescent units corrected for basal fluorescence as measured in the absence of glutamate. All data are calculated as relative $IC_{50}$ values using a four-parameter logistic curve fitting program (Activity Base® v5.3.1.22).

In the above assay, compounds exemplified herein exhibit an $IC_{50}$ of less than 750 nM at human $mGluR_5$. More specifically, the compound of Example 1 has an $IC_{50}$ of 184 nM measured at human $mGluR_5$. This demonstrates that compounds within the scope of the present invention are potent antagonists of $mGluR_5$.

Certain exemplified compounds have been evaluated at human $mGluR_1$. In the above assay, compounds of Examples 1-6, 8, 11, 20 and 22-28 exhibit an $IC_{50}$ of greater than 6000 nM at human $mGluR_1$. More specifically, the compound of Example 1 has an $IC_{50}$ greater than 12,500 nM measured at human $mGluR_1$. This demonstrates that compounds within the scope of the present invention are selective antagonists of $mGluR_5$ with respect to $mGluR_1$.

Anti-Parkinson effects of compounds of the invention can be determined using procedures well known in the art such as animal models of locomotor activity. For example, compounds of the invention show effects on basal (habituated) locomotor activity and on reserpine-induced akinesia in C57/black 6J male mice.

Basal (Habituated) Locomotor Activity

Locomotor activity is measured using an automated system to track movement in mice. Mice are placed in chambers and allowed to habituate to the chambers for 30 mins. During this time they show reduced locomotion over time. Following administration of a compound of the invention, animal movement is restored to pre-habituation levels.

More specifically, locomotor activity boxes [40×40×40 cm clear arenas] are situated in groups of 4 placed on infrared tables and testing is performed in the dark. Locomotor activity is recorded and measured using infrared video tracking. Locomotor activity is recorded between time of 8:30 and 17:00 hours. In some instances locomotor activity is measured using open fields which use infrared beam breaks as a measure of movement.

Mice are randomly assigned to treatment groups. Each mouse is placed individually into one of the locomotor activity boxes. Distance moved (cm) is recorded per 5 minutes for each mouse. Exploratory behavior is assessed for the following 30 minutes. After 30 minutes recording stops and mice are dosed p.o. with the test compound or vehicle in a volume of 10 ml/kg. Once all mice have been dosed, locomotor activity recording is started for a further 120 minutes to assess the effect of treatment on habituated locomotor activity. Data is transferred from the software/computers to spreadsheets for further analysis. Statistical analysis is carried out using Statistica 8.0. One way ANOVA on TOTAL distance moved, with Treatment group as the between factor, is calculated. If a significant Treatment effect ($p \leq 0.05$) is observed then post-hoc analysis is performed, either Fishers' LSD or Dunnetts' test.

In the above assay, the below Example compounds facilitate movement in mice in a dose responsive manner. This demonstrates that compounds within the scope of the present invention are effective in an in vivo model of Parkinson's disease.

| Test Compound | Basal Locomotor Activity (mean distance moved (cm) in 120 min) |
|---|---|
| Example 1 | |
| vehicle | 3886 |
| 1 mg/kg | 12147 ** |
| 3 mg/kg | 15980 *** |
| 10 mg/kg | 25109 *** |
| Example 3 | |
| vehicle | 8525.0 |
| 3 mg/kg | 28458.8 *** |
| 10 mg/kg | 39857.5 *** |
| Example 4 | |
| vehicle | 15729.4 |
| 3 mg/kg | 30715.2 ** |
| 10 mg/kg | 39935.6 *** |
| Example 27 | |
| vehicle | 15729.4 |
| 3 mg/kg | 35290.1 *** |
| 10 mg/kg | 36889.1 *** |
| Example 28 | |
| vehicle | 12886.3 |
| 3 mg/kg | 25074.1 ** |
| 10 mg/kg | 32866.2 *** |
| Example 23 | |
| vehicle | 8525.0 |
| 3 mg/kg | 21628.2 ** |
| 10 mg/kg | 31070.8 *** |

\* $p < 0.05$,
\*\* $p < 0.01$,
\*\*\* $p < 0.001$ compared to vehicle

Reversal of Reserpine-Induced Akinesia

Reserpine is a catecholamine depleting agent (depletes dopamine and noradrenaline) and 18-24 hours after treatment mice become akinetic and have reduced locomotor activity counts. Reserpine-induced akinesia is assessed by measuring the effect of compounds on locomotor activity approximately 18-24 hours after a single dose of 1 mg/kg reserpine i.p. The equipment used is the same as that used for basal locomotor activity (above).

Mice are randomly assigned to treatment groups. Each mouse is placed individually into one of the locomotor activity boxes. Distance moved (cm) is recorded per 5 minutes for each mouse. Basal and reserpine-induced exploratory behavior is assessed for the following 30 minutes. After 30 minutes recording stops and mice are dosed p.o. with the test compound in a volume of 10 ml/kg. Once all mice have been dosed locomotor activity recording is started for a further 120 minutes to assess the effect of treatment on akinesia. Data is transferred from the software/computers to spreadsheets for further analysis. Statistical analysis is carried out using Statistica 8.0. One way ANOVA on TOTAL distance moved, with Treatment group as the between factor, is calculated. If a significant Treatment effect ($p \leq 0.05$) is observed then post-hoc analysis is performed, either Fishers' LSD or Dunnetts' test.

In the above assay, the below Example compounds reverse the effects of reserpine and restore movement in mice in a dose responsive manner. This demonstrates that compounds within the scope of the present invention are effective in an in vivo model of Parkinson's disease.

| Test Compound | Reversal of Reserpine-Induced Akinesia (mean distance moved (cm) in 120 min) |
|---|---|
| Example 1 | |
| vehicle | 9240 |
| reserpine | 6150 |
| reserpine + 1 mg/kg | 15392 ++ |
| reserpine + 3 mg/kg | 23611 ***+++ |
| reserpine + 30 mg/kg | 32607 ***+++ |
| Example 4 | |
| vehicle | 9419.9 |
| reserpine | 4118.6 |
| reserpine + 3 mg/kg | 16474.1 + |
| reserpine + 10 mg/kg | 23394.4± **+++ |

-continued

| Test Compound | Reversal of Reserpine-Induced Akinesia (mean distance moved (cm) in 120 min) |
|---|---|
| Example 27 | |
| vehicle | 11590.0 |
| reserpine | 7331.1 |
| reserpine + 3 mg/kg | 27053.7 ***+++ |
| reserpine + 10 mg/kg | 23432.5 **+++ |
| Example 28 | |
| vehicle | 7715.9 |
| reserpine | 4597.2 |
| reserpine + 3 mg/kg | 7848.9 |
| reserpine + 10 mg/kg | 14087.6 **+++ |

* $p < 0.05$,
** $p < 0.01$,
*** $p < 0.001$ compared to vehicle
+ $p < 0.05$,
++ $p < 0.01$,
+++ $p < 0.001$ compared to reserpine Attenuation of Stress-Induced Hyperthermia in Rats Hyperthermia, a rise in core body temperature, is a general phenomenon that has been reliably demonstrated in many species in response to stress, and is a component of the well-characterized fight-or-flight response. Stress-induced hyperthermia is attenuated by clinical anxiolytics and is widely used preclinically to predict anxiolytic efficacy of compounds.

In separate studies, male Fischer F-344 Sasco rats are dosed orally with 0.3, 1, 3, or 10 mg/kg of test compound in a vehicle consisting of 1% carboxymethylcellulose, 0.25% polysorbate 80, 0.05% antifoam (dose volume=1 ml/kg). The mGluR$_5$ receptor antagonist MTEP (3-[(2-methyl-1,3-thiazol-4-yl)ethynyl]pyridine) (10 mg/kg, PO) is used as a quality control. Following a 60-min pretreatment period, core baseline body temperature is measured (T1, in degrees C.) and then ten minutes later a second body temperature measurement is recorded (T2). The change in body temperature (T2 minus T1) is defined as the stress-induced hyperthermic response. The efficacious dose is the dose at which a compound produces a 35% reduction in stress-induced hyperthermia, relative to the vehicle response, and is defined as the T35 dose.

In the above assay, the compound of Example 1 produces a reduction in stress-induced hyperthermia with a T35 dose=0.55 mg/kg. The compound of Example 3 produces a reduction in stress-induced hyperthermia with a T35 dose=0.93 mg/kg. This demonstrates that compounds within the scope of the present invention are effective in an in vivo model of anxiety.

Mouse Forced-Swim

Male, NIH-Swiss mice (20-25 g, Harlan Sprague-Dawley, Indianapolis, Ind.) are used in a method modified from that of Porsolt R D, Le Pichon M, Jalfre M Depression: a new animal model sensitive to antidepressant treatments. *Nature.* 1977 Apr. 21; 266(5604):730-2. Mice are placed in clear plastic cylinders (diameter 10 cm; height: 25 cm) filled to 6 cm with 22-25° C. water for six min. The duration of immobility is recorded during the last 4 min of a six-minute trial. A mouse is regarded as immobile when floating motionless or making only those movements necessary to keep its head above the water. Data are analyzed by post-hoc Dunnett's test with alpha level set at 0.05. The amount of time spent immobile is measured. Means+S.E.M. are subjected to ANOVA followed by Dunnett's test with $p < 0.05$ set as the error rate for statistical significance. ED60 values are extrapolated from the linear portion of the dose-effect curve and represent the dose predicted to decrease basal immobility (100% at 0 mg/kg compound) by 60%. The maximal decrease in immobility time is calculated using the largest decrease in immobility produced at any dose of a compound with this formula: (100-immobility with compound/immobility under vehicle control) %.

In the above assay, the compound of Example 1 produces a reduction in forced swim immobility with an ED60 dose=8.6 mg/kg and a maximal decrease in immobility of 50.6%. This demonstrates that compounds within the scope of the present invention are useful in an in vivo model of depression.

Compounds of formula I may be prepared by processes known in the chemical art for the production of structurally analogous compounds or by a novel process described herein. A process for the preparation of a compound of formula I, or a pharmaceutically acceptable salt thereof, and novel intermediates for the manufacture of a compound of formula I provide further features of the invention and are illustrated by the following procedures in which the meaning of substituents, such as $R^1$, $R^2$, $R^3$, and $R^4$, are as defined above, unless otherwise specified.

Generally, a compound of formula I may be prepared from a compound of formula II where $X^1$ is a suitable coupling group (Scheme 1). In a particular route, a compound of formula II where $X^1$ is a halo group such as bromo is reacted with a $R^3$-3-oxopiperazine-1-carboxylate and a suitable metal catalyst such as copper(I) iodide in the presence of a base such as potassium phosphate and an amine ligand such as N,N'-dimethylethylene diamine in a suitable solvent to provide a compound of formula I. Suitable solvents include 1,4-dioxane and dimethylformamide.

Alternatively, a compound of formula I may be prepared from a compound of formula II via a compound of formula III (Scheme 1). More specifically, a compound of formula II where $X^1$ is a halo group such as bromo is reacted with a 1-Pg-3-oxopiperazine where Pg is a suitable amine protecting group such as tert-butyloxycarbonyl and a suitable metal catalyst such as copper(I) iodide in the presence of a base such as potassium phosphate and an amine ligand such as N,N'-dimethylethylene diamine in a suitable solvent to provide a compound of formula IV where Pg is tert-butyloxycarbonyl. Suitable solvents include 1,4-dioxane and dimethylformamide. A compound of formula IV is reacted with a suitable deprotection agent such as hydrogen chloride or trifluoroacetic acid in a solvent to provide a compound of formula III. Suitable solvents include dichloromethane and ethyl acetate. A compound of formula III is acylated in a solvent with a $R^3$-carbonochloridate in the presence of a base such as triethylamine to provide a compound of formula I. Suitable solvents include dichloromethane.

Scheme 1

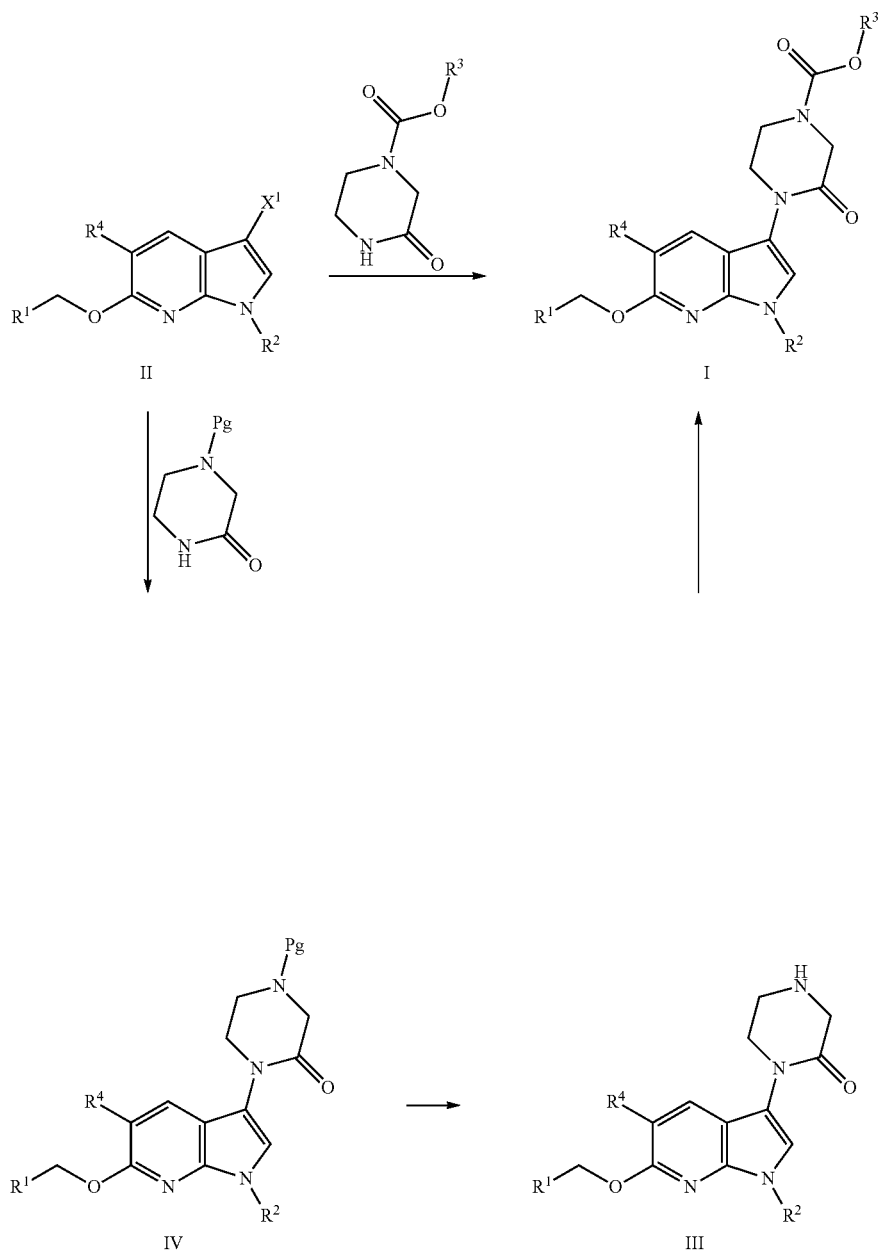

In Scheme 2, a compound of formula II may be prepared from a compound of formula V where $X^2$ is a suitable leaving group and $X^1$ is previously defined. More specifically, a compound of formula V where $X^2$ is a halo group such as fluoro is reacted in a solvent with $R^1CH_2OH$ in the presence of suitable base to provide a compound of formula II. Suitable bases include sodium hydride and potassium tert-butoxide. Suitable solvents include dimethylsulfoxide and dimethylformamide.

In a route alternative to Scheme 1, a compound of formula IV may be prepared from a compound of formula V (Scheme 2). More specifically, a compound of formula V where $X^1$ and $X^2$ are previously defined is reacted with a 1-Pg-3-oxopiperazine where Pg is a suitable amine protecting group such as tert-butyloxycarbonyl and a suitable metal catalyst such as copper(I) iodide in the presence of a suitable base such as potassium phosphate and an amine ligand such as N,N'-dimethylethylene diamine in a solvent to provide a compound of formula VI where Pg is tert-butyloxycarbonyl. Suitable solvents include 1,4-dioxane and dimethylformamide. A compound of formula VI where $X^2$ is a halo group such as fluoro is reacted in a suitable solvent with $R^1CH_2OH$ in the presence of suitable base to provide a compound of formula IV. Suitable bases include sodium hydride and potassium tert-butoxide. Suitable solvents include dimethylsulfoxide and dimethylformamide. A compound of formula V where $X^1$ and $X^2$ are previously defined may be prepared as described in the preparations or by procedures known in the chemical art for the production of structurally analogous compounds.

Scheme 2

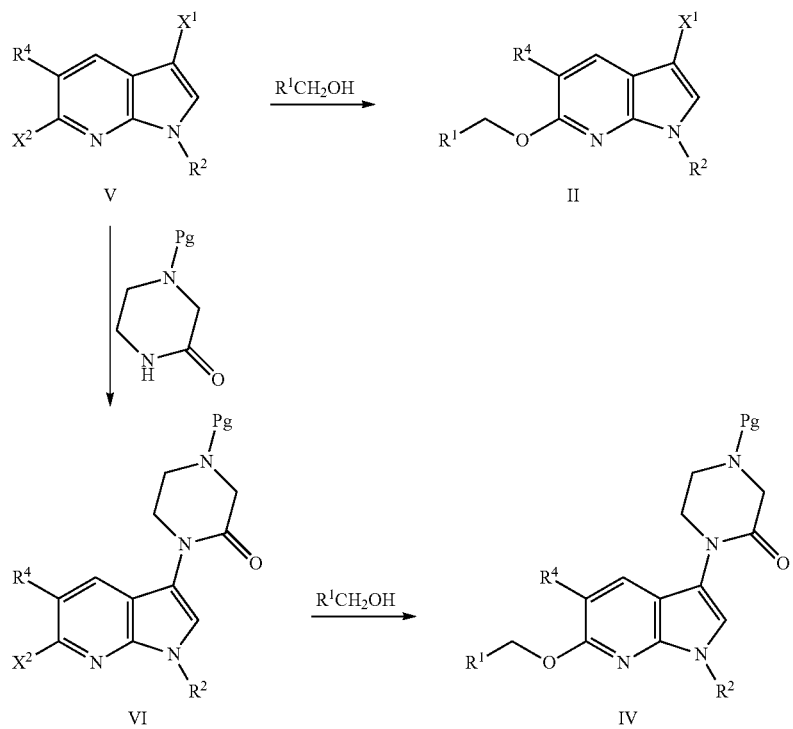

In the following illustrative preparations and examples, the following meanings and abbreviations are used throughout: DMSO, dimethyl sulfoxide (perdeuterated [-$d_6$] if for NMR); DSC, Differential scanning calorimetry; MS, mass spectrum; EtOAc, ethyl acetate; THF, tetrahydrofuran; min, minutes; h, hours; HPLC, high pressure liquid chromatography; LCMS, HPLC-mass spectrography; GC, gas chromatography; DMF, dimethylformamide; $Et_2O$, diethylether; DCM, dichloromethane; MeOH, methanol; MTBE, methyl t-butyl ether; SCX-2, cation exchange resin; mp, melting point; NMR, nuclear magnetic resonance spectroscopy or spectrum; SFC, supercriticial fluid chromatography; DMEA, dimethylethylamine; and $CHCl_3$, chloroform. Reagents were obtained from a variety of commercial sources. Solvents are generally removed under reduced pressure (evaporated). In some procedures indicated yields are representative crude yields for products which are isolated by evaporation or filtration and used directly without further purification.

Preparation 1

Synthesis of 6-fluoro-1-methyl-1H-pyrrolo[2,3-b]pyridine

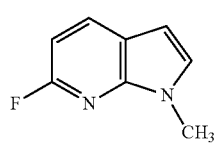

To a solution of 6-fluoro-1H-pyrrolo[2,3-b]pyridine (250 g, 1.84 mol) in dimethylformamide (2.50 L) is added potassium carbonate (507.6 g; 3.67 mol), followed by methyl iodide (171.6 mL, 2.75 mol). The reaction is stirred at room temperature overnight. The reaction mixture is poured into water (3000 mL) and extracted with $Et_2O$ (3×1500 mL). The organic extracts are combined and washed with water (4×1000 mL), then brine, and dried over $Na_2SO_4$. The solvent is evaporated to give a light brown oil which, on standing, gives clear colorless crystals, with a little mobile liquid on top of the crystals. The liquid is decanted off and discarded to leave the product as a crystalline solid (257.3 g, 1.71 moles). $^1$H-NMR (400 MHz, $CDCl_3$): δ 7.93 (t, 1H), 7.11 (d, 1H), 6.69 (d, 1H), 6.46 (d, 1H), 3.83 (s, 3H).

Preparation 2

Synthesis of 3-bromo-6-fluoro-1-methyl-pyrrolo[2,3-b]pyridine

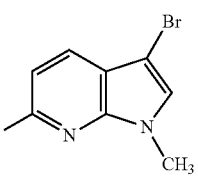

To a solution of 6-fluoro-1-methyl-1H-pyrrolo[2,3-b]pyridine (257.3 g, 1.71 mol) in DCM (3.86 L) is added N-bromosuccinimide (320.3 g; 1.80 mol) in five portions over 30 minutes. The mixture is stirred without heating or cooling overnight, then filtered and concentrated to about 1 L. This is purified by column chromatography on silica, eluting with 0 to 30% EtOAc in isohexane. The appropriate fractions are evaporated to give the product as an off white solid (391.3 g, 1.7 mol). $^{1}$H-NMR (400 MHz, CDCl$_3$): δ 7.91-7.87 (m, 1H), 7.15 (s, 1H), 6.77 (d, 1H), 3.81 (s, 3H).

Preparation 3

Synthesis of 3-bromo-1-methyl-6-(pyridin-2-yl-methoxy)-1H-pyrrolo[2,3-b]pyridine

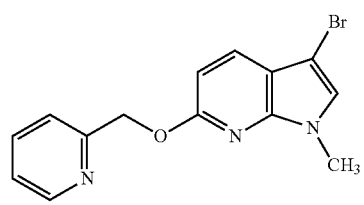 [SMILES: Cn1cc(Br)c2ccc(OCc3ccccn3)nc21]

Potassium tert-butoxide (137.4 g; 1.19 mol) and DMF (1.44 L) are charged into a flask, and a solution of 2-pyridyl-methanol (145.8 g, 1.34 mol) in DMF (306 mL) is added over 15 min. The flask is cooled as necessary to maintain room temperature. The mixture is stirred at room temperature for 40 minutes. A solution of 3-bromo-6-fluoro-1-methyl-pyrrolo[2,3-b]pyridine (170 g, 742.2 mmol) in DMF (306 mL) is added over 15 min., maintaining the temperature between 20 and 25° C. The mixture is stirred for 2 h. Water (1.7 L) is added slowly to the mixture, cooling as necessary, followed by extraction with EtOAc (4×1.0 L). The combined extracts are washed with water (4×1.0 L), then brine, and dried over sodium sulphate, filtered and concentrated to leave the product as a yellow solid (235.1 g, 0.74 moles). MS (m/z): 318.0/320.0.

Preparation 4

Synthesis of 3-bromo-1-methyl-6-(pyridin-4-yl-methoxy)-1H-pyrrolo[2,3-b]pyridine

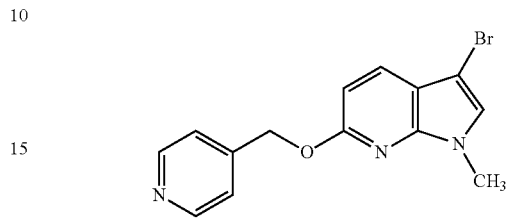

To a solution of 3-bromo-6-fluoro-1-methyl-1H-pyrrolo[2,3-b]pyridine (0.4 g, 1.74 mmol) and pyridine-4-ylmethanol (0.21 g, 1.93 mmol) in DMF (5.0 mL) is added portionwise sodium hydride (0.05 g, 2.11 mmol) at room temperature and the resulting reaction mixture is stirred for 1 h. The reaction is quenched with cold brine solution and extracted with EtOAc (4×100 mL). The combined organic layers are dried over sodium sulphate, filtered and concentrated in vacuo. The residue is purified by crystallization from Et$_2$O/pentane to give the title compound (0.300 g, 0.942 mmol) as an orange-red solid. MS (m/z): 318, 320 (M+1). $^{1}$H-NMR (400 MHz, DMSO-d$_6$): δ 3.73 (s, 3H), 5.48 (s, 2H), 6.76 (d, 1H), 7.47 (d, 2H), 7.50 (s, 1H), 7.78 (d, 1H), 8.56 (d, 2H).

The following compounds are prepared essentially by the method of Preparation 4.

| Preparation No. | Chemical Name | Structure | Physical Data |
|---|---|---|---|
| 5 | 3-Bromo-1-methyl-6-(pyridin-3-ylmethoxy)-1H-pyrrolo[2,3-b]pyridine | 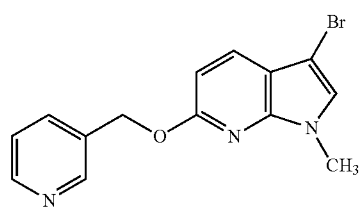 [SMILES: Cn1cc(Br)c2ccc(OCc3cccnc3)nc21] | MS (m/z): 318, 320 (M + 1). $^{1}$H-NMR (400 MHz, DMSO-d$_6$): δ 3.75 (s, 3H), 5.46 (s, 2H), 6.72 (d, 1H), 7.39-7.47 (d, 1H), 7.50 (s, 1H), 7.75 (d, 1H), 7.92-7.94 (m, 1H), 8.52-8.54 (m, 1H), 8.74(bs, 1H). |
| 6 | 3-Bromo-1-methyl-6-[(5-methylpyridin-2-yl)methoxy]-1H-pyrrolo[2,3-b]pyridine | 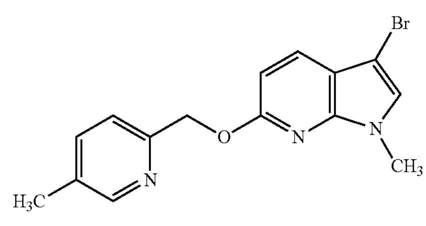 [SMILES: Cc1ccc(COc2ccc3c(Br)cn(C)c3n2)nc1] | MS (m/z): 332, 334 (M + 1). $^{1}$H-NMR (400 MHz, DMSO-d$_6$): δ: 2.29 (s, 3H),3.70 (s, 3H), 5.45 (s, 2H), 6.73 (d, 1H), 7.42 (d, 1H),7.48 (s, 1H), 7.60-7.62 (m, 1H), 7.76 (d, 1H), 8.40 (s, 1H). |
| 7 | 3-Bromo-1-methyl-6-[(3-methylpyridin-2-yl)methoxy]-1H-pyrrolo[2,3-b]pyridine | 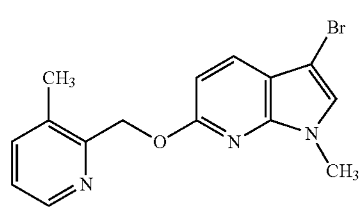 [SMILES: Cc1cccnc1COc1ccc2c(Br)cn(C)c2n1] | MS (m/z): 332, 334 (M + 1). $^{1}$H-NMR (400 MHz, DMSO-d$_6$): δ 2.39 (s, 3H), 3.73 (s, 3H), 5.48 (s, 2H), 6.68 (d, 1H), 7.26-7.29 (m, 1H), 7.49 (s, 1H), 7.64 (d, 1H), 7.75 (d, 1H), 8.37(d, 1H). |

| Preparation No. | Chemical Name | Structure | Physical Data |
|---|---|---|---|
| 8 | 3-Bromo-1-methyl-6-[(6-methylpyridin-2-yl)methoxy]-1H-pyrrolo[2,3-b]pyridine | 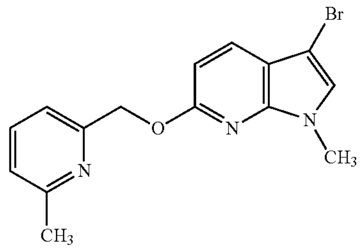 [SMILES: Cc1cccc(COc2ccc3c(Br)cn(C)c3n2)n1] | MS (m/z): 332, 334 (M + 1). $^1$H-NMR (400 MHz, DMSO-$d_6$): δ 2.47 (s, 3H), 3.70 (s, 3H), 5.44 (s, 2H), 6.75 (d, 1H), 7.18 (d, 1H), 7.30 (d, 1H), 7.48 (s, 1H), 7.68 (t, 1H), 7.77 (dd, 1H). |
| 9 | 3-Bromo-6-[(5-methoxypyridin-2-yl)methoxy]-1-methyl-1H-pyrrolo[2,3-b]pyridine | 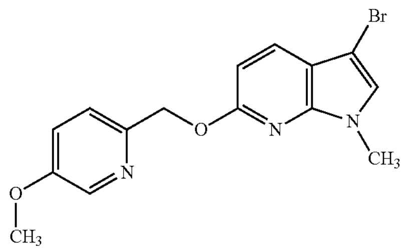 [SMILES: COc1ccc(COc2ccc3c(Br)cn(C)c3n2)nc1] | MS (m/z): 348, 350 (M + 1). |
| 10 | 3-Bromo-6-[(5-fluoropyridin-2-yl)methoxy]-1-methyl-1H-pyrrolo[2,3-b]pyridine | 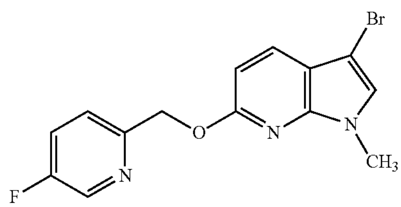 [SMILES: Cn1cc(Br)c2ccc(OCc3ccc(F)cn3)nc21] | MS (m/z): 336, 338 (M + 1). $^1$H-NMR (400 MHz, DMSO-$d_6$): δ 3.70 (s, 3H), 5.48 (s, 2H), 6.74 (d, 1H), 7.49 (s, 1H), 7.62 (dd, 1H), 7.72-7.77 (m, 1H), 7.78 (d, 1H), 8.56-8.57 (m, 1H). |
| 11 | 3-Bromo-1-ethyl-6-(pyridin-4-ylmethoxy)-1H-pyrrolo[2,3-b]pyridine | 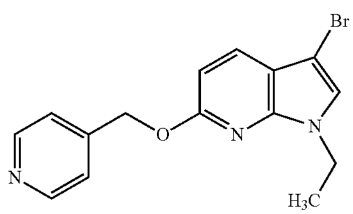 [SMILES: CCn1cc(Br)c2ccc(OCc3ccncc3)nc21] | MS (m/z): 332, 334 (M + 1). $^1$H-NMR (400 MHz, DMSO-$d_6$): δ 1.27 (t, 3H), 4.15 (q, 2H), 5.47 (s, 2H), 6.76 (d, 1H), 7.46 (d, 2H), 7.56 (s, 1H), 7.77 (d, 1H), 8.55 (d, 2H). |
| 12 | 3-Bromo-1-ethyl-6-[(5-methylpyridin-2-yl)methoxy]-1H-pyrrolo[2,3-b]pyridine | 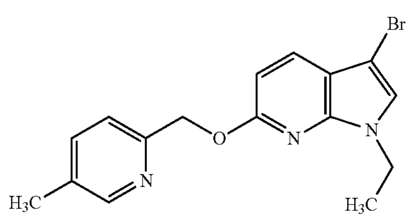 [SMILES: CCn1cc(Br)c2ccc(OCc3ccc(C)cn3)nc21] | MS (m/z): 346, 348 (M + 1). |

Preparation 13

Synthesis of ethyl 3-oxopiperazine-1-carboxylate

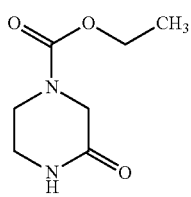

To a solution of 2-piperazinone (5.0 g, 50.0 mmol) and triethylamine (11.09 g, 110.0 mmol) in DCM (15 mL) is added ethyl chloroformate (5.9 g, 55.0 mmol) at room temperature and the reaction mixture is stirred for 2 h. The reaction is quenched with water (100 mL) and extracted with DCM (3×100 mL). The combined organic layers are dried over anhydrous sodium sulphate, filtered and concentrated in vacuo. The residue is triturated with Et$_2$O to give the title compound (5.0 g, 29.05 mmol) as a pale yellow solid. $^1$H-NMR (400 MHz, DMSO-$d_6$): δ 1.19 (t, 3H), 3.16-3.19 (m, 2H), 3.48-3.51 (m, 2H), 3.85 (s, 2H), 4.05 (q, 2H), 8.06 (s, 1H).

The following compounds are prepared essentially by the method of Preparation 13.

| Preparation No. | Chemical Name | Structure | Physical Data |
|---|---|---|---|
| 14 | Methyl-3-oxopiperazine-1-carboxylate | 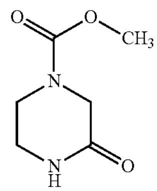 | MS (m/z): 159 (M + 1). |
| 15 | Propyl 3-oxopiperazine-1-carboxylate | 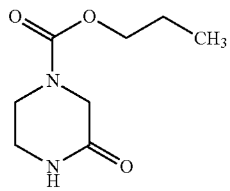 | MS (m/z): 187 (M + 1).<br>¹H-NMR (400 MHz, DMSO-$d_6$): δ 0.89 (t, 3H), 1.54-1.63 (m, 2H), 3.16-3.20 (m, 2H), 3.50 (m, 2H), 3.86 (s, 2H), 3.97 (t, 2H), 8.06 (s, 1H). |
| 16 | Propan-2-yl 3-oxopiperazine-1-carboxylate | 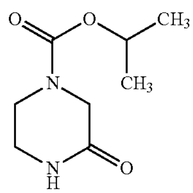 | MS (m/z): 187 (M + 1).<br>¹H-NMR (400 MHz, DMSO-$d_6$) : δ 1.19 (d, 6H), 3.16-3.19 (m, 2H), 3.47-3.50 (m, 2H), 3.84 (s, 2H), 4.79 (m, 1H), 8.04 (s, 1H). |

Preparation 17

Synthesis of 1-cyclopropyl-6-fluoro-1H-pyrrolo[2,3-b]pyridine

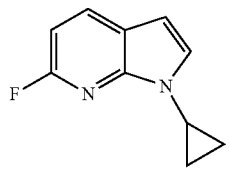 [SMILES: Fc1ccc2ccn(C3CC3)c2n1]

To a solution of 6-fluoro-1H-pyrrolo[2,3-b]pyridine (6.2 g, 45.55 mmol) in dry DCM (250 mL) is added cyclopropylboronic acid (7.82 g, 91.09 mmol), followed by cupric acetate (8.36 g, 45.55 mmol), sodium carbonate (9.65 g, 91.09 mmol) and 2,2'-bipyridine (7.11 g, 45.55 mmol). The resulting mixture is stirred and heated at 50° C. for 15 h. The mixture is cooled to room temperature and further cupric acetate (4.18 g, 22.77 mmol) and sodium carbonate (2.41 g, 22.77 mmol) are added, followed by cyclopropylboronic acid (1.96 g, 22.77 mmol). The mixture is stirred and heated at 50° C. for a further 15 h when further cupric acetate (1.5 g, 8.25 mmol) and cyclopropylboronic acid (1.49 g, 17.34 mmol) are added. The mixture is stirred at room temperature for 4 days and then poured onto sat. aq. NH₄Cl, diluted with water and extracted with DCM. The organic layers are combined, washed with brine, dried (magnesium sulphate) and concentrated in vacuo to give a green oil, which is purified by column chromatography on silica, eluting with DCM, to give the title compound (2.03 g, 11.52 mmol). MS (m/z): 177 (M+1). Unreacted 6-fluoro-1H-pyrrolo[2,3-b]pyridine is also recovered (3.012 g, 22.1 mmol). MS (m/z): 137 (M+1).

Preparation 18

Synthesis of 3-bromo-1-cyclopropyl-6-fluoro-1H-pyrrolo[2,3-b]pyridine

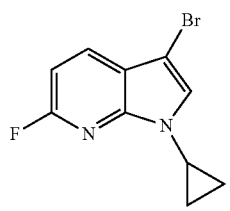 [SMILES: Fc1ccc2c(Br)cn(C3CC3)c2n1]

To a solution of 1-cyclopropyl-6-fluoro-1H-pyrrolo[2,3-b]pyridine (2.03 g, 11.52 mmol) in DMF (38 mL) is added sodium hydroxide (0.506 g, 12.67 mmol), followed by N-bromosuccinimide (2.26 g, 12.67 mmol) portionwise over 5 minutes, resulting in an exothermic reaction (28° C.). The mixture is stirred at room temperature for 15 min., and further sodium hydroxide (46.1 mg, 1.15 mmol) and N-bromosuccinimide (0.205 g, 1.15 mmol) are added. Stirring is continued at room temperature for 30 min. Further sodium hydroxide (46.1 mg, 1.15 mmol) and N-bromosuccinimide (0.205 g, 1.15 mmol) are added. The reaction mixture is stirred at room temperature for 16 h and then poured onto brine (ca. 500 mL) and extracted with CHCl₃ (ca. 2×300 mL). The organic layers are combined and dried over magnesium sulphate, filtered, and concentrated in vacuo to give a brown oil, which is purified by column chromatography on silica, eluting with 0 to 100% DCM in isohexane, to give the title compound as a white powder (2.32 g, 9.10 mmol). MS (m/z): 255/257 (M+1).

Preparation 19

Synthesis of 3-bromo-1-cyclopropyl-6-(pyridin-2-ylmethoxy)-1H-pyrrolo[2,3-b]pyridine

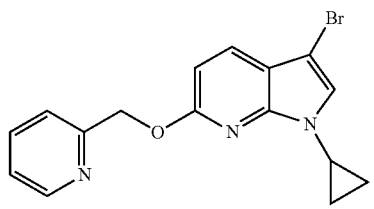 [SMILES: Brc1cn(C2CC2)c2nc(OCc3ccccn3)ccc12]

To a solution of 3-bromo-1-cyclopropyl-6-fluoro-1H-pyrrolo[2,3-b]pyridine (0.249 g, 0.98 mmol) in dimethyl sulfoxide (5 mL) is added 2-pyridinemethanol (188 µL, 1.95 mmol), followed by portionwise addition of sodium hydride (97.6 mg, 2.44 mmol). The mixture is stirred at room temperature for 5 min., then poured onto brine and extracted with EtOAc. The organic layers are combined, dried (magnesium sulphate) and concentrated in vacuo to give a brown oil. This is taken up in methanol and poured onto a SCX-2 ion-exchange column. This is washed with 3 column volumes of MeOH, and then the product collected in the subsequent one column volume flush with 7 M methanolic ammonia. The solution is then concentrated in vacuo to give the title compound as a yellow oil (0.263 g, 0.76 mmol). MS (m/z): 344/346 (M+1).

Preparation 20

Synthesis of tert-butyl 4-[1-methyl-6-(pyridin-2-ylmethoxy)-1H-pyrrolo[2,3-b]pyridin-3-yl]-3-oxopiperazine-1-carboxylate

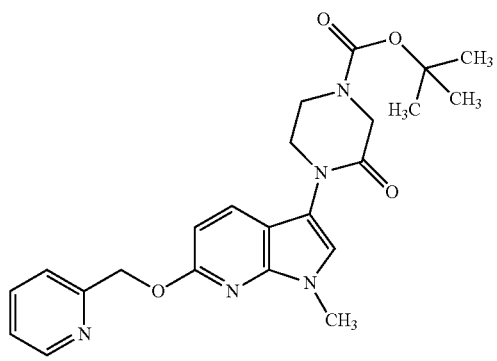 [SMILES: Cn1cc(N2CCN(C(=O)OC(C)(C)C)CC2=O)c2ccc(OCc3ccccn3)nc21]

A mixture of 3-bromo-1-methyl-6-(pyridin-2-ylmethoxy)-1H-pyrrolo[2,3-b]pyridine (0.226 g, 0.71 mmol), tert-butyl 3-oxopiperazine-1-carboxylate (0.20 g, 1 mmol), copper (I) iodide (0.027 g, 0.142 mmol) and potassium phosphate (0.212 g, 1 mmol) is purged under a nitrogen atmosphere in a reaction tube. 1,4-Dioxane (3 mL) and N,N'-dimethylethylene diamine (0.031 mL, 0.288 mmol) are added, the tube sealed and the reaction mixture heated at 100° C. for 25 h. The reaction is cooled to room temperature, poured into water and extracted with EtOAc. The organic phase is dried over sodium sulphate, filtered and concentrated in vacuo. The residue is purified by column chromatography on silica eluting with hexane/EtOAc (1:1), followed by neat EtOAc, to give the title compound (0.275 g, 0.629 mmol) as a pale yellow solid. MS (m/z): 438 (M+1).

Preparation 21

Synthesis of 1-[1-methyl-6-(pyridin-2-ylmethoxy)-1H-pyrrolo[2,3-b]pyridin-3-yl]piperazin-2-one, hydrochloride

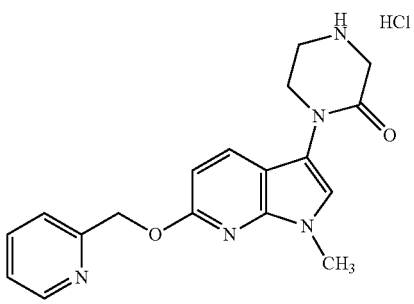 [SMILES: Cl ; Cn1cc(N2CCNCC2=O)c2ccc(OCc3ccccn3)nc21]

To a solution of tert-butyl 4-[1-methyl-6-(pyridin-2-ylmethoxy)-1H-pyrrolo[2,3-b]pyridin-3-yl]-3-oxopiperazine-1-carboxylate (0.278 g, 0.653 mmol) in DCM (10 mL) is added a saturated solution of hydrogen chloride in EtOAc (6 mL) at room temperature, and the reaction mixture stirred at room temperature for 67 h. The solvent is carefully decanted off and the residue triturated with Et₂O/MeOH. The solvent is again decanted off and the residue further triturated with Et₂O/MeOH. The resultant residue is dried in vacuo for 3 h. to give the title compound (0.217 g, 0.580 mmol) as a pale yellow solid. MS (m/z): 338 (M+1).

Preparation 22

Synthesis of cyclobutyl carbonochloridate

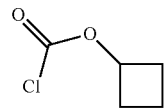

To a solution of cyclobutanol (5.0 g, 69.4 mmol) and pyridine (5.4 g, 69.4 mmol) in DCM (30 mL) is added portionwise triphosgene (10.2 g, 34.7 mmol) at 0° C. The reaction mixture is warmed to room temperature and stirred for 3 h. The reaction is quenched with 10% aqueous solution of sulfuric acid (100 mL) and extracted with DCM (5×100 mL). The combined organic layers are dried over sodium sulphate, filtered and concentrated in vacuo to afford the title compound (4.1 g, 30.47 mmol) as a colorless viscous oil, contaminated with starting alcohol. The material is used in the next step without further purification. ¹H-NMR (400 MHz, CDCl₃): δ 1.57-1.64 (m, 2H), 2.06-2.16 (m, 2H), 2.31-2.38 (m, 2H), 4.85-4.93 (m, 1H).

Preparation 23

Synthesis of 1-ethyl-6-fluoro-1H-pyrrolo[2,3-b]pyridine

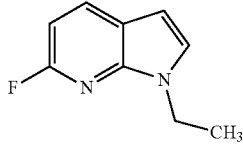

To a stirred solution of 6-fluoro-1H-pyrrolo[2,3-b]pyridine (15.00 g, 110.19 mmol) in DMF (100 mL), under a nitrogen atmosphere, is added potassium carbonate (22.84 g, 165.3 mmol), followed by ethyl bromide (12.36 mL, 165.3 mmol). The reaction is heated to 70° C. for 4 h. Further ethyl bromide (3.00 mL, 27.6 mmol) is added and the reaction kept at 70° C. overnight. After cooling further potassium carbonate (8.00 g, 57.9 mmol) and ethyl bromide (3.00 mL, 27.6 mmol) are added, and the reaction heated at 70° C. for 4 h. The reaction is cooled, poured onto brine (ca. 500 mL) and the product extracted with CHCl₃ (ca. 2×300 mL). The combined organic extracts are dried over magnesium sulphate, filtered, and concentrated in vacuo to give a brown oil. This is purified by column chromatography on silica, eluting with 0 to 70% DCM in hexane to give the title compound as a light yellow oil (16.38 g, 99.77 mmol). MS (m/z): 165 (M+1).

Preparation 24

Synthesis of 3-bromo-1-ethyl-6-fluoro-1H-pyrrolo[2,3-b]pyridine

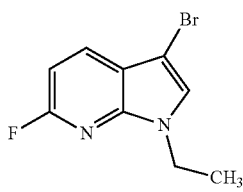

A solution of 1-ethyl-6-fluoro-1H-pyrrolo[2,3-b]pyridine (16.38 g, 99.77 mmol) in DMF (300 mL) is cooled to 15° C. with stirring. To this is added sodium hydroxide (4.39 g, 109.7 mmol), followed by N-bromosuccinimide (19.53 g, 109.7 mmol) portionwise over 5 minutes, and then the reaction is allowed to stir at room temperature overnight. The reaction is poured onto brine (ca. 500 mL) and the product extracted with CHCl₃ (ca. 2×300 mL). The combined organic phase is dried over magnesium sulphate, filtered, and concentrated in vacuo to give a brown oil. This is purified by column chromatography on silica, eluting with 0 to 60% DCM in hexane, to give the title compound as a light yellow oil (23.4 g, 96.4 mmol). MS (m/z): 243/245 (M+1).

Preparation 25

Synthesis of tert-butyl 4-(1-ethyl-6-fluoro-1H-pyrrolo[2,3-b]pyridin-3-yl)-3-oxopiperazine-1-carboxylate

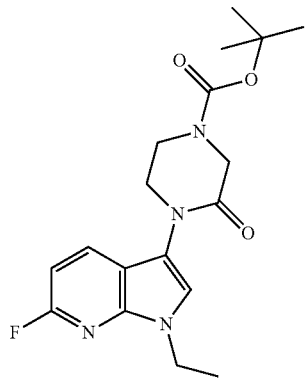 [SMILES: CCn1cc(N2CCN(C(=O)OC(C)(C)C)CC2=O)c2ccc(F)nc21]

3-Bromo-1-ethyl-6-fluoro-1H-pyrrolo[2,3-b]pyridine (13.00 g, 53.48 mmol), tert-butyl 3-oxopiperazine-1-carboxylate (11.78 g, 58.83 mmol), N,N'-dimethylethane-1,2-diamine (2.36 mL, 21.93 mmol), copper(I) iodide (2.24 g, 11.77 mmol), potassium phosphate (tribasic, n-hydrate) (12.49 g, 58.83 mmol), and 1,4-dioxane (250 mL) are combined under a nitrogen atmosphere with stirring and heated to reflux overnight. The reaction is cooled, poured onto brine (ca. 500 mL) and the product extracted with CHCl₃ (ca. 2×300 mL). The combined organic extracts are dried over magnesium sulphate, filtered, and concentrated in vacuo to give a yellow oil. This is purified by column chromatography on silica, eluting with 0 to 90% EtOAc in hexane, to give the title compound as an orange oil (20.039 g, 55.29 mmol). MS (m/z): 363 (M+1).

Preparation 26

Synthesis of tert-butyl 4-[1-ethyl-6-(pyridin-2-yl-methoxy)-1H-pyrrolo[2,3-b]pyridin-3-yl]-3-oxopiperazine-1-carboxylate

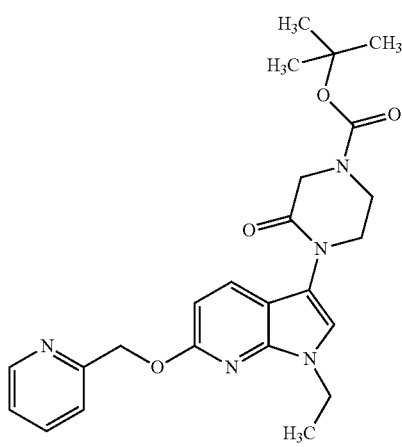 [SMILES: CCn1cc(N2CCN(C(=O)OC(C)(C)C)CC2=O)c2ccc(OCc3ccccn3)nc21]

To a stirred solution of tert-butyl 4-(1-ethyl-6-fluoro-1H-pyrrolo[2,3-b]pyridin-3-yl)-3-oxopiperazine-1-carboxylate (5.00 g, 13.80 mmol) and 2-pyridine methanol (1.60 mL, 16.56 mmol) in dimethyl sulphoxide (50 mL), under a nitrogen atmosphere, is added 60% sodium hydride (0.662 g, 16.56 mmol) portionwise. The reaction is stirred at room temperature for 1 h and then heated at 135° C. overnight. The reaction is cooled to room temperature and further 60% sodium hydride (0.662 g, 16.56 mmol) added, and the reaction stirred overnight at room temperature. The reaction is poured onto brine (ca. 500 mL) and the product extracted with CHCl₃ (ca. 2×300 mL). The combined organic extracts are dried over magnesium sulphate, filtered, and concentrated in vacuo to give a brown oil. This is purified by column chromatography on silica, eluting with 0 to 80% EtOAc in DCM, to give the title compound as an orange foam (4.952 g, 10.97 mmol). MS (m/z): 452 (M+1).

Preparation 27

Synthesis of 1-[1-ethyl-6-(pyridin-2-ylmethoxy)-1H-pyrrolo[2,3-b]pyridin-3-yl]piperazin-2-one

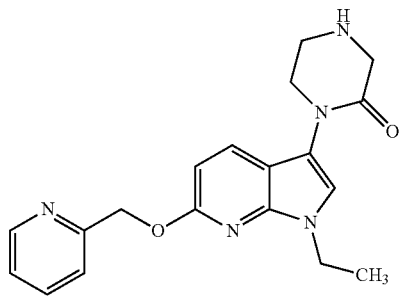 [SMILES: CCn1cc(N2CCNCC2=O)c2ccc(OCc3ccccn3)nc21]

To a stirred solution of tert-butyl 4-[1-ethyl-6-(pyridin-2-ylmethoxy)-1H-pyrrolo[2,3-b]pyridin-3-yl]-3-oxopiperazine-1-carboxylate (4.952 g, 10.97 mmol) in DCM (20 mL) is added trifluoroacetic acid (4.15 mL, 54.84 mmol) over 2 minutes and the reaction stirred for 90 minutes. The reaction is diluted with MeOH and poured on to a SCX2 ion-exchange column. This is flushed with one column volume of MeOH, and then the product collected in the subsequent one column volume flush of 7 M methanolic ammonia. This solution is then concentrated in vacuo to give a brown oil. This is purified by column chromatography on silica, eluting with 0 to 40% MeOH in EtOAc, to give the title compound as an orange oil (2.989 g, 8.51 mmol). MS (m/z): 352 (M+1).

Preparation 28

Synthesis of 5-fluoro-1H-pyrrolo[2,3-b]pyridine 7-oxide

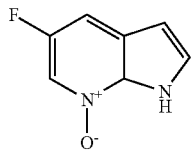 [SMILES: [O-][NH+]1C=C(F)C=C2C=CNC21]

To a stirred solution of 5-fluoro-1H-pyrrolo[2,3-b]pyridine (5.00 g, 36.73 mmol) in Et₂O (120 mL), under a nitrogen atmosphere, is added 3-chloroperoxybenzoic acid (11.09 g, 64.28 mmol) portionwise over 5 minutes and the reaction stirred for 3 h. The reaction is then cooled to 5° C., filtered and the solid washed with Et₂O (ca. 100 mL). This is dried in vacuo to give the title compound as a pale green crystalline solid (4.317 g, 28.38 mmol). MS (m/z): 153 (M+1).

The following compounds are prepared essentially by the method of Preparation 28.

| Prep. No. | Chemical name | Structure | Physical data |
|---|---|---|---|
| 29 | 5-Chloro-1H-pyrrolo[2,3-b]pyridine 7-oxide | 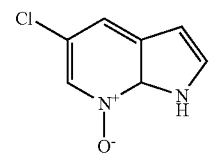 [SMILES: [O-][NH+]1C=C(Cl)C=C2C=CNC21] | MS (m/z): 169/171 (M + 1). |
| 30 | 5-Methyl-1H-pyrrolo[2,3-b]pyridine 7-oxide | 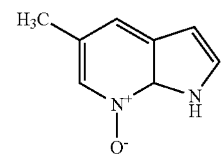 | MS (m/z): 149 (M + 1). |

Preparation 31

Synthesis of 6-chloro-5-fluoro-1H-pyrrolo[2,3-b]pyridine

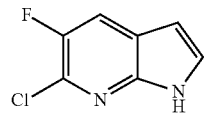 [SMILES: Fc1cc2cc[nH]c2nc1Cl]

To a stirred solution of 5-fluoro-1H-pyrrolo[2,3-b]pyridine 7-oxide (4.317 g, 28.38 mmol) in THF (150 mL) is added hexamethyldisilazane (6.54 mL, 31.22 mmol). The reaction mixture is cooled to 5° C. and methyl chloroformate (5.49 mL, 70.94 mmol) added dropwise. After stirring at 5° C. for 3 h, 2M sodium hydroxide (80 mL, 0.16 mol) is added dropwise, keeping temperature below 10° C. After 2 h, 2M hydrochloric acid solution is added until the mixture is at pH7. The reaction is poured onto brine (ca. 500 mL) and product extracted with CHCl₃ (ca. 4×300 mL). The combined organic extracts are dried over magnesium sulphate, filtered, and concentrated in vacuo to give the title compound as a light brown solid (4.15 g, 24.33 mmol). MS (m/z): 171/173 (M+1). The following compounds are prepared essentially by the method of Preparation 31.

| Preparation No. | Chemical name | Structure | Physical data |
| --- | --- | --- | --- |
| 32 | 5,6-Dichloro-1H-pyrrolo[2,3-b]pyridine | 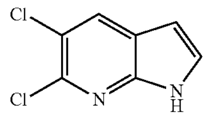 [SMILES: Clc1cc2cc[nH]c2nc1Cl] | MS (m/z): 187/189/191 (M + 1). |
| 33 | 6-Chloro-5-methyl-1H-pyrrolo[2,3-b]pyridine | 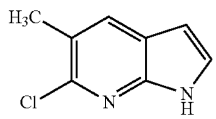 | MS (m/z): 167/169 (M + 1). |

Preparation 34

Synthesis of 6-chloro-5-fluoro-1-methyl-1H-pyrrolo[2,3-b]pyridine

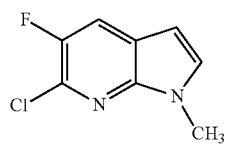

To a solution of 6-chloro-5-fluoro-1H-pyrrolo[2,3-b]pyridine (4.15 g, 24.33 mmol) in DMF (50 mL), under a nitrogen atmosphere, is added potassium carbonate (6.73 g, 48.66 mmol), followed by methyl iodide (2.27 mL, 36.49 mmol), and reaction heated to 70° C. for 2 h. The reaction is cooled, poured onto brine (ca. 50 mL) and the product extracted with CHCl₃ (ca. 2×30 mL). The combined organic extracts are dried over magnesium sulphate, filtered, and concentrated in vacuo to give a brown solid. This is purified by column chromatography on silica, eluting with 0 to 50% DCM in hexane, to give the title compound as a white solid (1.274 g, 6.90 mmol). MS (m/z): 185/187 (M+1).

The following compounds are prepared essentially by the method of Preparation 34.

Preparation 37

Synthesis of 5-fluoro-1-methyl-6-(pyridin-2-yl-methoxy)-1H-pyrrolo[2,3-b]pyridine

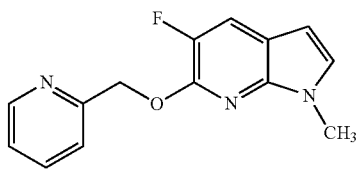

To a stirred solution of 6-chloro-5-fluoro-1-methyl-1H-pyrrolo[2,3-b]pyridine (1.276 g, 6.91 mmol) and 2-pyridine methanol (0.800 mL, 8.29 mmol) in dimethyl sulphoxide (10 mL), under a nitrogen atmosphere, is added 60% sodium hydride (0.332 g, 8.29 mmol) portionwise, and reaction stirred at room temperature overnight. The reaction is then heated to 80° C. for 1 h, cooled to room temperature and further 60% sodium hydride (0.090 g, 2.32 mmol) added. After 30 minutes of stirring at room temperature, the reaction is further heated at 80° C. for 30 minutes. The reaction is cooled, poured onto brine (ca. 50 mL) and the product extracted with CHCl₃ (ca. 2×30 mL). The combined organic extracts are dried over magnesium sulphate, filtered, and con-

| Preparation No. | Chemical name | Structure | Physical data |
| --- | --- | --- | --- |
| 35 | 5,6-Dichloro-1-methyl-1H-pyrrolo[2,3-b]pyridine | 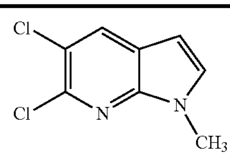 | MS (m/z): 201/203/205 (M + 1). |
| 36 | 6-Chloro-1,5-dimethyl-1H-pyrrolo[2,3-b]pyridine | | MS (m/z): 181/183 (M + 1). | centrated in vacuo to give a brown oil. This is purified by column chromatography on silica, eluting with 0 to 80% EtOAc in hexane, to give the title compound as a light green oil (1.445 g, 5.62 mmol). MS (m/z): 258 (M+1).

The following compounds are prepared essentially by the method of Preparation 37.

To a stirred solution of 5-fluoro-1-methyl-6-(pyridin-2-ylmethoxy)-1H-pyrrolo[2,3-b]pyridine (1.00 g, 3.89 mmol) in DMF (30 mL), cooled to 15° C. under a nitrogen atmosphere, is added sodium hydroxide (0.171 g, 4.28 mmol), followed by N-bromosuccinimide (0.761 g, 4.28 mmol) portionwise over 5 minutes. After 15 minutes, the reaction is

| Preparation No. | Chemical name | Structure | Physical data |
|---|---|---|---|
| 38 | 5-Chloro-1-methyl-6-(pyridin-2-ylmethoxy)-1H-pyrrolo[2,3-b]pyridine | 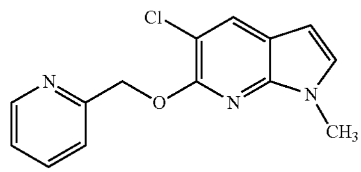 [SMILES: Cn1ccc2cc(Cl)c(OCc3ccccn3)nc21] | MS (m/z): 274/276 (M + 1). |
| 39 | 1,5-Dimethyl-6-(pyridin-2-ylmethoxy)-1H-pyrrolo[2,3-b]pyridine | 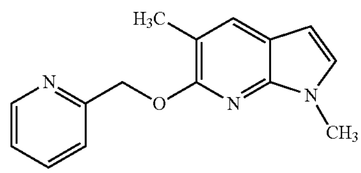 [SMILES: Cc1cc2ccn(C)c2nc1OCc1ccccn1] | MS (m/z): 254 (M + 1). |

Preparation 40

Synthesis of 3-bromo-5-fluoro-1-methyl-6-(pyridin-2-ylmethoxy)-1H-pyrrolo[2,3-b]pyridine

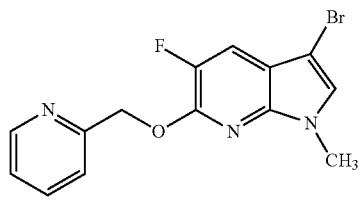 [SMILES: Cn1cc(Br)c2cc(F)c(OCc3ccccn3)nc21]

poured onto brine (ca. 50 mL) and the product extracted with CHCl₃ (ca. 2×30 mL). The combined organic extracts are dried over magnesium sulphate, filtered, and concentrated in vacuo to give a brown oil. This is purified by column chromatography on silica, eluting with 0 to 100% EtOAc in hexane, to give the title compound as a light yellow solid (1.195 g, 3.55 mmol). MS (m/z): 336/338 (M+1).

The following compounds are prepared essentially by the method of Preparation 40.

| Preparation No. | Chemical name | Structure | Physical data |
|---|---|---|---|
| 41 | 3-Bromo-5-chloro-1-methyl-6-(pyridin-2-ylmethoxy)-1H-pyrrolo[2,3-b]pyridine | 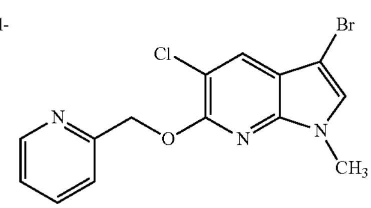 | MS (m/z): 352/354/356 (M + 1). |
| 42 | 3-Bromo-1,5-dimethyl-6-(pyridin-2-ylmethoxy)-1H-pyrrolo[2,3-b]pyridine | 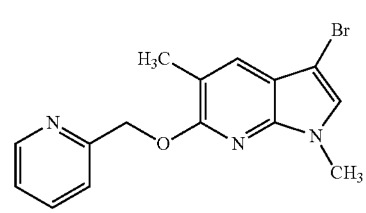 [SMILES: Cc1cc2c(Br)cn(C)c2nc1OCc1ccccn1] | MS (m/z): 332/334 (M + 1). |

Example 1

Synthesis of ethyl 4-[1-methyl-6-(pyridin-2-yl-methoxy)-1H-pyrrolo[2,3-b]pyridin-3-yl]-3-oxopiperazine-1-carboxylate

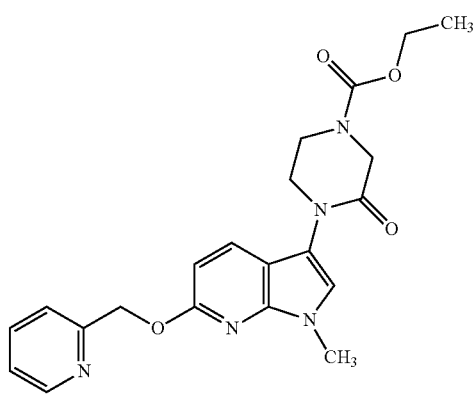 [SMILES: CCOC(=O)N1CCN(c2cn(C)c3nc(OCc4ccccn4)ccc23)C(=O)C1]

Ethyl 3-oxo-piperazine-1-carboxylate (161.4 g, 937.2 mmol), copper(I) iodide (27.65 g, 145.20 mmol) and potassium phosphate (tribasic, n-hydrate) (205.1 g, 937.2 mmol) is charged into a glass reactor at room temperature under nitrogen. A solution of 3-bromo-1-methyl-6-(pyridin-2-yl-methoxy)-1H-pyrrolo[2,3-b]pyridine (210 g, 660.0 mmol) in 1,4-dioxane (2.73 L) is added, followed by N,N'-dimethyl-ethane-1,2-diamine (24.34 g; 270.6 mmol). The reaction mixture is heated to 100° C. and stirred for 20 h. Further copper(I) iodide (10.06 g, 52.80 mmol) and N,N'-dimethylethane-1,2-diamine (10.95 g, 105.6 mmol) is added and the reaction stirred for a further 23 h. The reaction mixture is combined with a smaller batch made in a similar manner starting with 23.68 g of 3-bromo-1-methyl-6-(pyridin-2-ylmethoxy)-1H-pyrrolo[2,3-b]pyridine. The mixture is cooled to room temperature, then poured into water (4.2 L) and extracted with EtOAc (3×1.7 L). The organic extracts are combined and washed with 3% w/w aqueous ammonia (3×400 mL), then water (2×2 L), then brine (600 mL), and dried over sodium sulphate, filtered and concentrated in vacuo. The residue is purified by column chromatography on silica, eluting with 50 to 100% EtOAc in isohexane. The appropriate fractions are combined, evaporated and recrystallized from ethanol (525 mL). The solid is dried to give the title compound (125.6 g, 0.3 mol). MS (m/z): 410.1 (M+1). $^1$H-NMR (400 MHz, CDCl$_3$): δ 1.31 (t, 3H), 3.72 (s, 3H), 3.80-3.78 (t, 2H), 3.86 (t, 2H), 4.22 (q, 2H), 4.34 (s, 2H), 5.59 (s, 2H), 6.71 (d, 1H), 7.01 (s, 1H), 7.20 (dd, 1H), 7.49 (d, 1H), 7.70-7.66 (m, 2H), 8.60 (d, 1H). DSC (onset) mp=143.42° C.

Further material is obtained by flushing the chromatography column with a large amount of EtOAc and evaporating the appropriate fractions. Recrystallization of the residue from ethanol (100 mL) gives an additional batch of the title compound (26.29 g, 64.26 mmol).

Alternative synthesis of ethyl 4-[1-methyl-6-(pyridin-2-ylmethoxy)-1H-pyrrolo[2,3-b]pyridin-3-yl]-3-oxopiperazine-1-carboxylate To a solution of 1-[1-methyl-6-(pyridin-2-ylmethoxy)-1H-pyrrolo[2,3-b]pyridin-3-yl]piperazin-2-one, hydrochloride (0.10 g, 0.267 mmol) and triethylamine (160 µL, 1.148 mmol) in DCM (1.5 mL) is added dropwise ethyl carbonochloridate (35 µL, 0.366 mmol) at room temperature and the reaction mixture is stirred for 1.5 h. The reaction is poured into water and extracted with DCM. After separation, the organic layer is dried over sodium sulphate, filtered and concentrated in vacuo. The residue is purified on silica gel (10 g Isolute cartridge), eluting with EtOAc, to afford a very dense pale yellow oil, which solidified upon addition of Et$_2$O. The material is triturated in Et$_2$O, filtered off and washed twice with Et$_2$O, to afford the title compound (0.066 g, 0.161 mmol) as a colorless solid. MS (m/z) 410 (M+1).

Example 2

Synthesis of methyl 4-[1-methyl-6-(pyridin-2-yl-methoxy)-1H-pyrrolo[2,3-b]pyridin-3-yl]-3-oxopiperazine-1-carboxylate

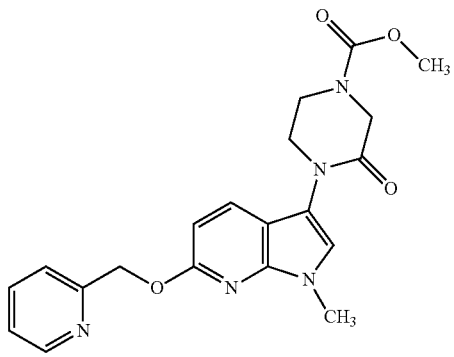 [SMILES: COC(=O)N1CCN(c2cn(C)c3nc(OCc4ccccn4)ccc23)C(=O)C1]

To a solution of 3-bromo-1-methyl-6-(2-pyridylmethoxy) pyrrolo[2,3-b]pyridine (0.5 g, 1.57 mmol) in 1,4-dioxane (10 mL) is added methyl 3-oxopiperazine-1-carboxylate (0.271 g, 1.88 mmol) and potassium phosphate (0.467 g, 2.20 mmol). The mixture is degassed with nitrogen for 15 minutes, then copper(I) iodide (0.060 g, 0.31 mmol) and N,N'-dimethylethylenediamine (0.055 g, 0.63 mmol) are added. The reaction vessel is sealed and heated at 100° C. for 16 h. The reaction is cooled to room temperature, quenched with water (50 mL) and extracted with EtOAc (3×100 mL). The combined organic layers are dried over anhydrous sodium sulphate, filtered and concentrated in vacuo. The residue is purified by column chromatography on neutral alumina, eluting with 1% MeOH in DCM. The resultant product is triturated with Et$_2$O/pentane (1:1) to afford the title compound (0.5 g, 1.26 mmol) as an off white solid. MS (m/z): 396 (M+1). $^1$H-NMR (400 MHz, DMSO-d$_6$): δ 3.66 (s, 3H), 3.68 (s, 3H), 3.75 (m, 4H), 4.14 (s, 2H), 5.49 (s, 2H), 6.66 (d, 1H), 7.30-7.33 (m, 2H), 7.50 (d, 1H), 7.77-7.82 (m, 2H), 8.56 (d, 1H).

The following compounds are prepared essentially by the method of Example 2.

| Example No. | Chemical Name | Structure | Physical data |
|---|---|---|---|
| 3 | Propyl 4-[1-methyl-6-(pyridin-2-ylmethoxy)-1H-pyrrolo[2,3-b]pyridin-3-yl]-3-oxopiperazine-1-carboxylate | 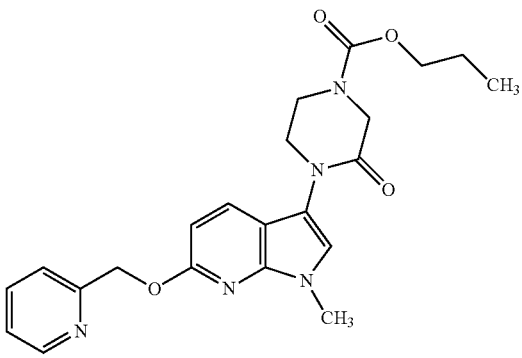 [SMILES: CCCOC(=O)N1CCN(c2cn(C)c3nc(OCc4ccccn4)ccc23)C(=O)C1] | MS (m/z): 424 (M + 1).<br>$^1$H-NMR (400 MHz, DMSO-$d_6$): δ 0.92 (t, 3H), 1.59-1.64 (m, 2H), 3.68 (s, 3H), 3.75 (m, 4H), 4.02 (t, 2H), 4.14 (s, 2H), 5.49 (s, 2H), 6.66 (d, 1H), 7.30-7.34 (m, 2H), 7.50 (d, 1H), 7.77-7.82 (m, 2H), 8.56 (d, 1H). |
| 4 | 1-Methylethyl 4-[1-methyl-6-(pyridin-2-ylmethoxy)-1H-pyrrolo[2,3-b]pyridin-3-yl]-3-oxopiperazine-1-carboxylate | 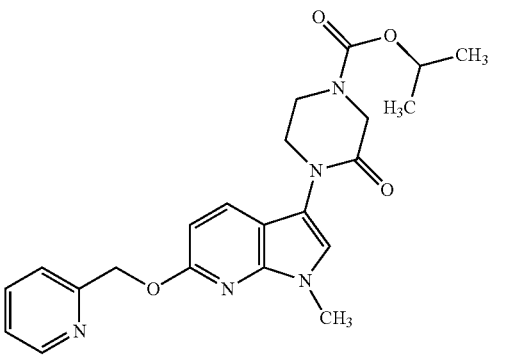 [SMILES: CC(C)OC(=O)N1CCN(c2cn(C)c3nc(OCc4ccccn4)ccc23)C(=O)C1] | MS (m/z): 424 (M + 1).<br>$^1$H-NMR (400 MHz, DMSO-$d_6$): δ 1.23 (d, 6H), 3.68 (s, 3H), 3.74 (m, 4H), 4.13 (s, 2H), 4.80-4.86 (m, 1H), 5.49 (s, 2H), 6.66 (d, 1H), 7.30-7.33 (m, 1H), 7.34 (s, 1H), 7.50 (d, 1H), 7.77-7.82 (m, 2H), 8.56 (d, 1H). |
| 5 | Ethyl 4-[1-methyl-6-(pyridin-4-ylmethoxy)-1H-pyrrolo[2,3-b]pyridin-3-yl]-3-oxopiperazine-1-carboxylate | 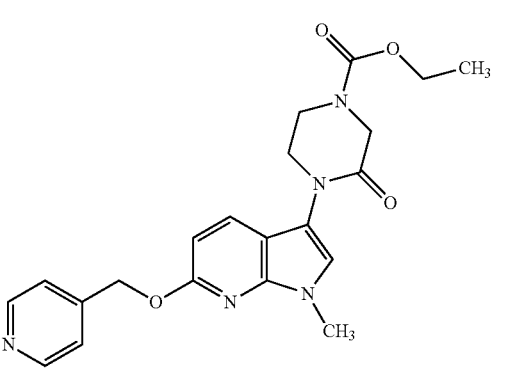 [SMILES: CCOC(=O)N1CCN(c2cn(C)c3nc(OCc4ccncc4)ccc23)C(=O)C1] | MS (m/z): 410 (M + 1).<br>$^1$H-NMR (400 MHz, DMSO-$d_6$): δ 1.22 (t, 3H), 3.69 (s, 3H), 3.74 (m, 4H), 4.04-4.14 (m, 4H), 5.48 (s, 2H), 6.67 (d, 1H), 7.34 (s, 1H), 7.47 (d, 2H), 7.81 (d, 1H), 8.55 (bs, 2H). |
| 6 | Ethyl 4-[1-methyl-6-(pyridin-3-ylmethoxy)-1H-pyrrolo[2,3-b]pyridin-3-yl]-3-oxopiperazine-1-carboxylate | 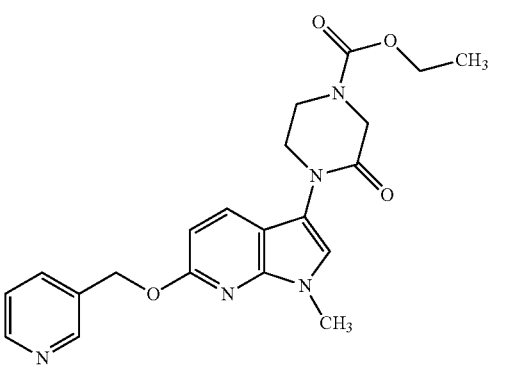 [SMILES: CCOC(=O)N1CCN(c2cn(C)c3nc(OCc4cccnc4)ccc23)C(=O)C1] | MS (m/z): 410(M + 1).<br>$^1$H-NMR (400 MHz, DMSO-$d_6$): δ 1.22 (t, 3H), 3.74 (m, 7H), 4.07-4.12 (m, 4H), 5.46 (s, 2H), 6.60 (d, 1H), 7.35 (s, 1H), 7.39-7.42 (m, 1H), 7.79 (d, 1H), 7.92 (d, 1H), 8.52 (bs, 1H), 8.74 (bs, 1H). |

| Example No. | Chemical Name | Structure | Physical data |
|---|---|---|---|
| 7 | Ethyl 4-{6-[(5-fluoropyridin-2-yl)methoxy]-1-methyl-1H-pyrrolo[2,3-b]pyridin-3-yl}-3-oxopiperazine-1-carboxylate | 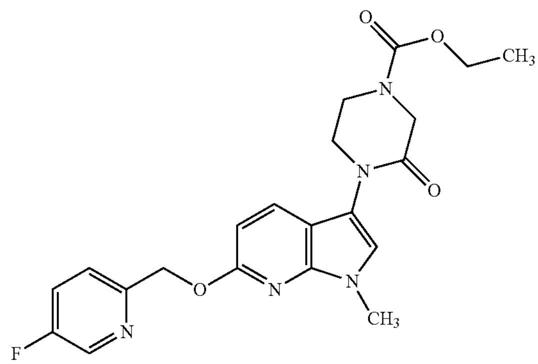 [SMILES: CCOC(=O)N1CCN(c2cn(C)c3nc(OCc4ccc(F)cn4)ccc23)C(=O)C1] | MS (m/z): 428 (M + 1). $^1$H-NMR (400 MHz, DMSO-$d_6$): δ 1.22 (t, 3H), 3.68 (s, 3H), 3.75 (m, 4H), 4.07-4.14 (m, 4H), 5.49 (s, 2H), 6.65 (d, 1H), 7.34 (s, 1H), 7.58-7.62 (m, 1H), 7.73 (td, 1H), 7.81 (d, 1H), 8.56 (bd, 1H). |
| 8 | Ethyl 4-{1-methyl-6-[(5-methylpyridin-2-yl)methoxy]-1H-pyrrolo[2,3-b]pyridin-3-yl}-3-oxopiperazine-1-carboxylate | 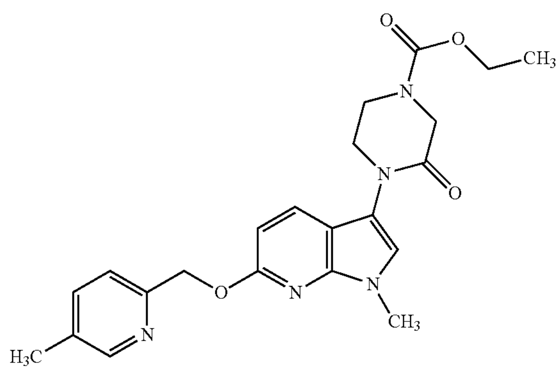 [SMILES: CCOC(=O)N1CCN(c2cn(C)c3nc(OCc4ccc(C)cn4)ccc23)C(=O)C1] | MS (m/z): 424 (M + 1). $^1$H-NMR (400 MHz, DMSO-$d_6$): δ 1.22 (t, 3H), 2.28 (s, 3H), 3.69 (s, 3H), 3.75 (m, 4H), 4.08-4.14 (m, 4H), 5.44 (s, 2H), 6.64 (d, 1H), 7.33 (s, 1H), 7.41 (d, 1H), 7.61 (d, 1H), 7.80 (d, 1H), 8.39 (s, 1H). |
| 9 | Ethyl 4-{6-[(5-methoxypyridin-2-yl)methoxy]-1-methyl-1H-pyrrolo[2,3-b]pyridin-3-yl}-3-oxopiperazine-1-carboxylate | 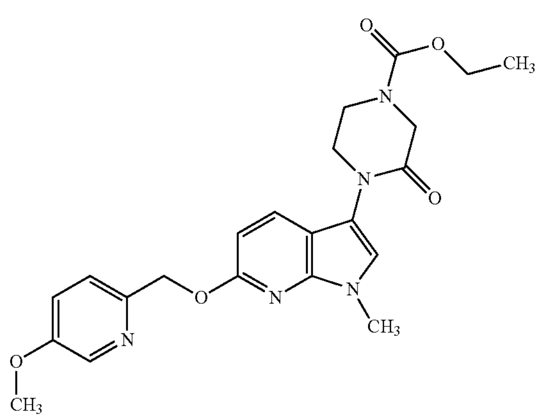 [SMILES: CCOC(=O)N1CCN(c2cn(C)c3nc(OCc4ccc(OC)cn4)ccc23)C(=O)C1] | MS (m/z): 440 (M + 1). |
| 10 | Ethyl 4-{1-methyl-6-[(3-methylpyridin-2-yl)methoxy]-1H-pyrrolo[2,3-b]pyridin-3-yl}-3-oxopiperazine-1-carboxylate | 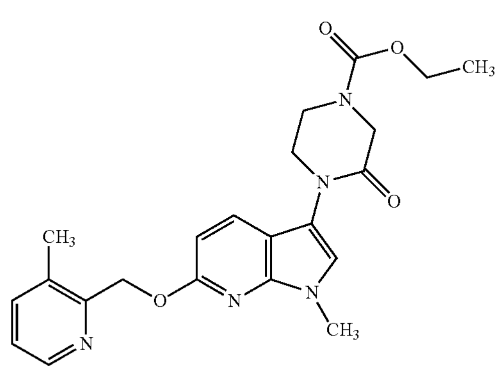 [SMILES: CCOC(=O)N1CCN(c2cn(C)c3nc(OCc4ncccc4C)ccc23)C(=O)C1] | MS (m/z): 424 (M + 1). $^1$H-NMR (400 MHz, DMSO-$d_6$): δ 1.22 (t, 3H), 2.39 (s, 3H), 3.72 (s, 3H), 3.75 (m, 4H), 4.07-4.14 (m, 4H), 5.48 (s, 2H), 6.58 (d, 1H), 7.28 (dd, 1H), 7.34 (s, 1H), 7.64 (d, 1H), 7.77 (d, 1H), 8.37 (d, 1H). |

-continued

| Example No. | Chemical Name | Structure | Physical data |
|---|---|---|---|
| 11 | Ethyl 4-{1-methyl-6-[(6-methylpyridin-2-yl)methoxy]-1H-pyrrolo[2,3-b]pyridin-3-yl}-3-oxopiperazine-1-carboxylate | 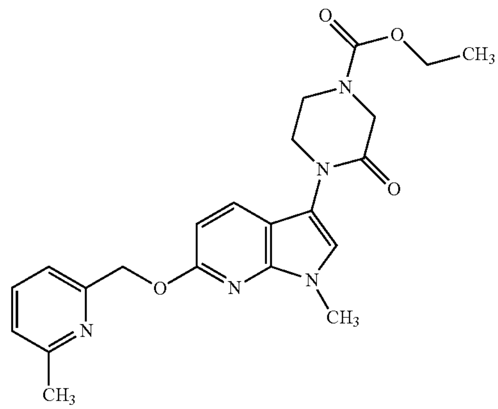 [SMILES: CCOC(=O)N1CCN(c2cn(C)c3nc(OCc4cccc(C)n4)ccc23)C(=O)C1] | MS (m/z): 424 (M + 1). <sup>1</sup>H-NMR (400 MHz, DMSO-d<sub>6</sub>): δ 1.22 (t, 3H), 2.47 (s, 3H), 3.69 (s, 3H), 3.75 (m, 4H), 4.09-4.14 (m, 4H), 5.44 (s, 2H), 6.66 (d, 1H), 7.17 (d, 1H), 7.29 (d, 1H), 7.34 (s, 1H), 7.68(t, 1H), 7.81 (d, 1H). |
| 12 | Methyl 4-{6-[(5-fluoropyridin-2-yl)methoxy]-1-methyl-1H-pyrrolo[2,3-b]pyridin-3-yl}-3-oxopiperazine-1-carboxylate | 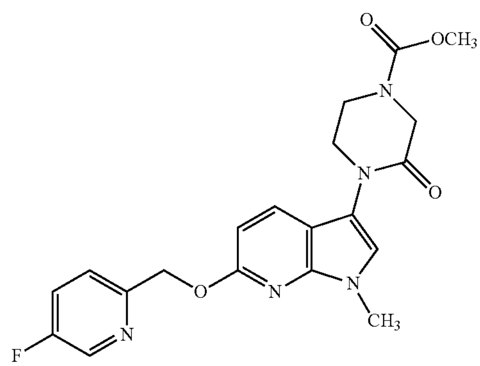 [SMILES: COC(=O)N1CCN(c2cn(C)c3nc(OCc4ccc(F)cn4)ccc23)C(=O)C1] | MS (m/z): 414 (M + 1). |
| 13 | Methyl 4-{1-methyl-6-[(5-methylpyridin-2-yl)methoxy]-1H-pyrrolo[2,3-b]pyridin-3-yl}-3-oxopiperazine-1-carboxylate | 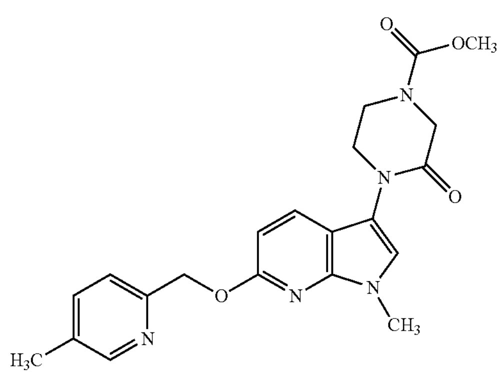 [SMILES: COC(=O)N1CCN(c2cn(C)c3nc(OCc4ccc(C)cn4)ccc23)C(=O)C1] | MS (m/z): 410 (M + 1). <sup>1</sup>H-NMR (400 MHz, DMSO-d<sub>6</sub>): δ 2.28 (s, 3H), 3.66 (s, 3H), 3.69 (s, 3H), 3.75 (m, 4H), 4.14 (s, 2H), 5.44 (s, 2H), 6.64 (d, 1H), 7.33 (s, 1H), 7.40 (d, 1H), 7.61 (d, 1H), 7.80 (d, 1H), 8.39 (s, 1H). |
| 14 | Methyl 4-{6-[(5-methoxypyridin-2-yl)methoxy]-1-methyl-1H-pyrrolo[2,3-b]pyridin-3-yl}-3-oxopiperazine-1-carboxylate | 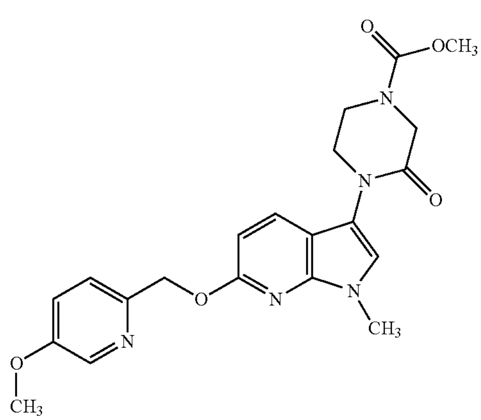 [SMILES: COC(=O)N1CCN(c2cn(C)c3nc(OCc4ccc(OC)cn4)ccc23)C(=O)C1] | MS (m/z): 426 (M + 1). |

-continued

| Example No. | Chemical Name | Structure | Physical data |
|---|---|---|---|
| 15 | Methyl 4-[1-methyl-6-(pyridin-4-ylmethoxy)-1H-pyrrolo[2,3-b]pyridin-3-yl]-3-oxopiperazine-1-carboxylate | 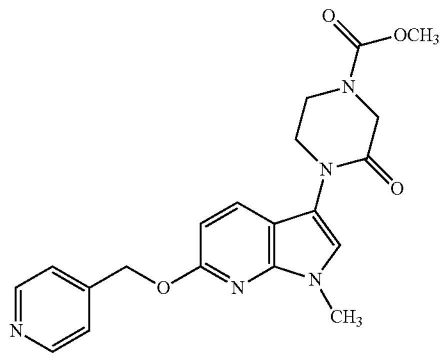 [SMILES: COC(=O)N1CCN(c2cn(C)c3nc(OCc4ccncc4)ccc23)C(=O)C1] | MS (m/z): 396 (M + 1). <br> $^1$H-NMR (400 MHz, DMSO-$d_6$): δ 3.66 (s, 3H), 3.69 (s, 3H), 3.75 (m, 4H), 4.14 (s, 2H), 5.48 (s, 2H), 6.67 (d, 1H), 7.34 (s, 1H), 7.47 (d, 2H), 7.81 (d, 1H), 8.55 (d, 2H). |
| 16 | Ethyl 4-[1-ethyl-6-(pyridin-4-ylmethoxy)-1H-pyrrolo[2,3-b]pyridin-3-yl]-3-oxopiperazine-1-carboxylate | 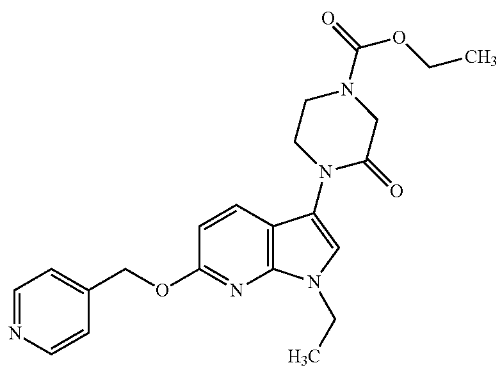 [SMILES: CCOC(=O)N1CCN(c2cn(CC)c3nc(OCc4ccncc4)ccc23)C(=O)C1] | MS (m/z): 424 (M + 1). <br> $^1$H-NMR (400 MHz, DMSO-$d_6$): δ 1.22 (t, 3H), 1.27 (t, 3H), 3.74 (m, 4H), 4.08-4.15 (m, 6H), 5.47 (s, 2H), 6.67 (d, 1H), 7.40 (s, 1H), 7.45 (d, 2H), 7.80 (d, 1H), 8.54 (d, 2H). |
| 17 | Methyl 4-[1-ethyl-6-(pyridin-4-ylmethoxy)-1H-pyrrolo[2,3-b]pyridin-3-yl]-3-oxopiperazine-1-carboxylate | 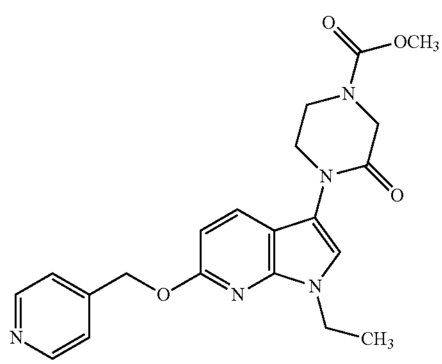 [SMILES: CCn1cc(N2CCN(C(=O)OC)CC2=O)c2ccc(OCc3ccncc3)nc21] | MS (m/z): 410 (M + 1). <br> $^1$H-NMR (400 MHz, DMSO-$d_6$) δ: 1.27 (t, 3H), 3.66 (s, 3H), 3.75 (m, 4H), 4.10-4.15 (m, 4H), 5.47 (s, 2H), 6.67 (d, 1H), 7.39 (s, 1H), 7.45 (d, 2H), 7.80 (d, 1H), 8.54 (d, 2H). |
| 18 | Methyl 4-{1-ethyl-6-[(5-methylpyridin-2-yl)methoxy]-1H-pyrrolo[2,3-b]pyridin-3-yl}-3-oxopiperazine-1-carboxylate | 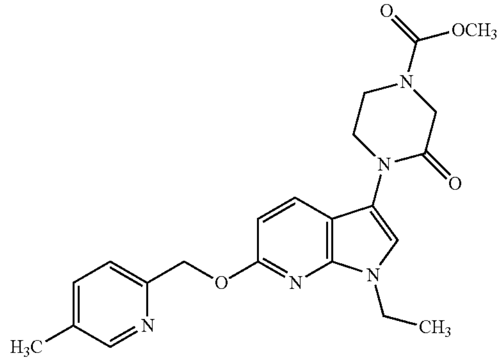 [SMILES: CCn1cc(N2CCN(C(=O)OC)CC2=O)c2ccc(OCc3ccc(C)cn3)nc21] | MS (m/z): 424 (M + 1). <br> $^1$H-NMR (400 MHz, DMSO-$d_6$): δ 1.29 (t, 3H), 2.27 (s, 3H), 3.66 (s, 3H), 3.75 (m, 4H), 4.12-4.15 (m, 4H), 5.43 (s, 2H), 6.63 (d, 1H), 7.37-7.39 (m, 1H), 7.39 (s, 1H), 7.59 (d, 1H), 7.78 (d, 1H), 8.39 (bs, 1H). |

Example 19

Synthesis of ethyl 4-[1-cyclopropyl-6-(pyridin-2-ylmethoxy)-1H-pyrrolo[2,3-b]pyridin-3-yl]-3-oxopiperazine-1-carboxylate

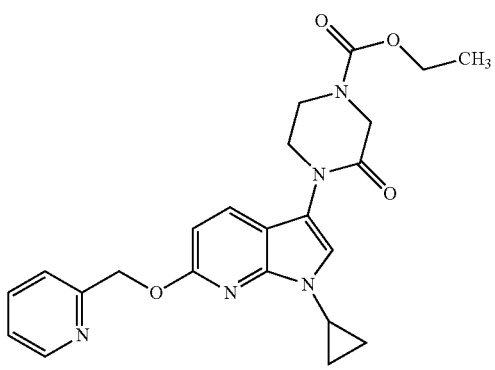 [SMILES: CCOC(=O)N1CCN(c2cn(C3CC3)c3nc(OCc4ccccn4)ccc23)C(=O)C1]

A mixture of 3-bromo-1-cyclopropyl-6-(pyridin-2-ylmethoxy)-1H-pyrrolo[2,3-b]pyridine (0.263 g, 765 μmol), ethyl 3-oxopiperazine-1-carboxylate (0.158 g, 0.918 mmol), N,N'-dimethylethane-1,2-diamine (33.8 μL, 0.313 mmol), copper(I) iodide (32 mg, 168 μmol), potassium phosphate (tribasic, n-hydrate) (0.179 g, 841 μmol) in DMF (10 mL) is heated at 120° C. for 15 h. The mixture is cooled to room temperature and further copper(I) iodide (0.145 g, 765 μmol), potassium phosphate (tribasic, n-hydrate) (0.536 g, 2.52 mmol) and N,N'-dimethylethane-1,2-diamine (165 μL, 1.53 mmol) are added, followed by ethyl 3-oxopiperazine-1-carboxylate (0.132 g, 0.765 mmol). After further heating for 24 h under nitrogen at 100° C., the mixture is concentrated in vacuo, diluted with MeOH and poured onto a SCX-2 ion-exchange column. This is washed with 3 column volumes of MeOH and then the product collected in the subsequent one column volume flush of 7 M methanolic ammonia. The solution is concentrated in vacuo and purified by column chromatography on silica, eluting with 0 to 100% EtOAc in isohexane, to give the title compound as a yellow oil (40 mg, 0.09 mmol). MS (m/z): 436 (M+1). $^1$H-NMR (400 MHz, CDCl$_3$): 0.89-0.99 (m, 4H), 1.31 (t, 3H), 3.31-3.37 (m, 1H), 3.76-3.78 (m, 2H), 3.82-3.88 (m, 2H), 4.22 (q, 2H), 4.33 (s, 2H), 5.60 (s, 2H), 6.72 (d, 1H), 7.00 (s, 1H), 7.18-7.22 (m, 1H), 7.48-7.52 (m, 1H), 7.64-7.69 (m, 2H), 8.59-8.61 (m, 1H).

Example 20

Synthesis of 2-fluoroethyl 4-[1-methyl-6-(pyridin-2-ylmethoxy)-1H-pyrrolo[2,3-b]pyridin-3-yl]-3-oxopiperazine-1-carboxylate

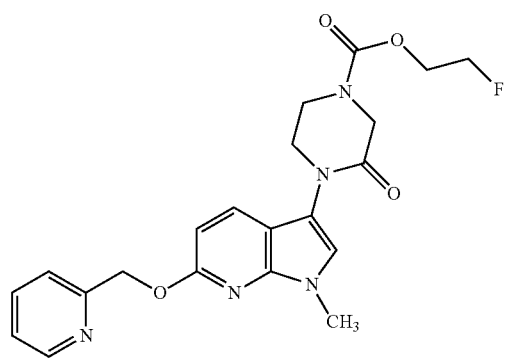 [SMILES: Cn1cc(N2CCN(C(=O)OCCF)CC2=O)c2ccc(OCc3ccccn3)nc21]

To a solution of 1-[1-methyl-6-(pyridin-2-ylmethoxy)-1H-pyrrolo[2,3-b]pyridin-3-yl]piperazin-2-one, hydrochloride (0.15 g, 0.40 mmol) and triethylamine (0.121 g, 1.20 mmol) in DCM (15 mL) is added dropwise 2-fluoroethyl carbonochloridate (0.076 g, 0.602 mmol) at room temperature, and the reaction mixture is stirred for 3 h. The reaction is quenched with a saturated solution of sodium bicarbonate (20 mL) at 0° C. and extracted with DCM (3×50 mL). The combined organic layers are dried over sodium sulphate, filtered and concentrated in vacuo. The residue is purified on neutral alumina, eluting with 1% MeOH in DCM to give a product, which on triturating in Et$_2$O, affords the title compound (0.07 g, 0.164 mmol) as an off-white solid. MS (m/z): 428 (M+1). $^1$H-NMR (400 MHz, DMSO-d$_6$): δ 3.68 (s, 3H), 3.77 (m, 4H), 4.17 (bs, 2H), 4.28 (t, 1H), 4.35 (t, 1H), 4.58 (t, 1H), 4.71 (t, 1H), 5.49 (s, 2H), 6.66 (d, 1H), 7.30-7.34 (m, 2H), 7.50 (d, 1H), 7.77-7.83 (m, 2H), 8.56 (d, 1H).

The following compounds are prepared essentially by the method of Example 20.

| Example No. | Chemical Name | Structure | Physical Data |
|---|---|---|---|
| 21 | 2-Methoxyethyl 4-[1-methyl-6-(pyridin-2-ylmethoxy)-1H-pyrrolo[2,3-b]pyridin-3-yl]-3-oxopiperazine-1-carboxylate | 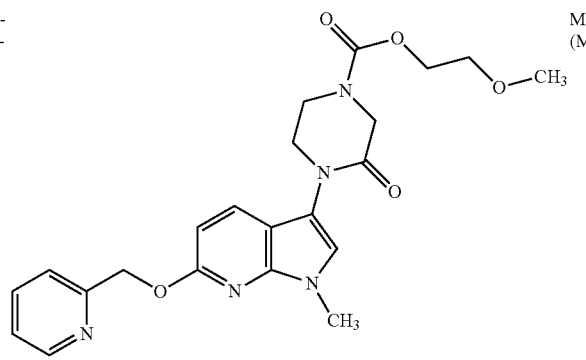 | MS (m/z): 440 (M + 1) |

| Example No. | Chemical Name | Structure | Physical Data |
|---|---|---|---|
| 22 | Cyclobutyl 4-[1-methyl-6-(pyridin-2-ylmethoxy)-1H-pyrrolo[2,3-b]pyridin-3-yl]-3-oxopiperazine-1-carboxylate | 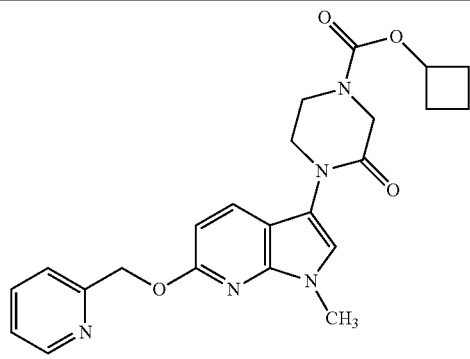 | MS (m/z): 436 (M + 1) |

Example 23

Synthesis of methyl 4-[1-ethyl-6-(pyridin-2-ylmethoxy)-1H-pyrrolo[2,3-b]pyridin-3-yl]-3-oxopiperazine-1-carboxylate

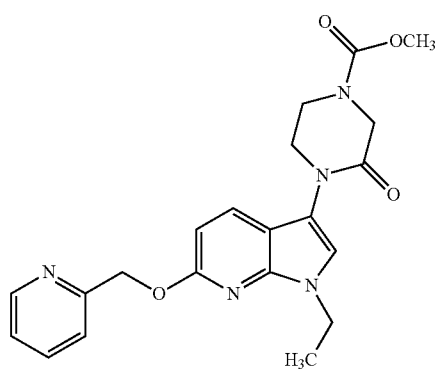 [SMILES: CCn1cc(N2CCN(C(=O)OC)CC2=O)c2ccc(OCc3ccccn3)nc21]

To a stirred solution of 1-[1-ethyl-6-(pyridin-2-ylmethoxy)-1H-pyrrolo[2,3-b]pyridin-3-yl]piperazin-2-one (0.200 g, 0.569 mmol) in DCM (10 mL) is added triethylamine (0.095 mL, 0.683 mmol), followed by methyl chloroformate (0.052 mL, 0.683 mmol). The reaction is then stirred overnight. The reaction is diluted with MeOH, and poured on to a SCX2 ion-exchange column. This is flushed with one column volume of MeOH, and then the product collected in the subsequent one column volume flush of 7 M methanolic ammonia. The solution is then concentrated in vacuo to give the title compound as an orange oil (0.1643 g, 0.401 mmol). MS (m/z): 410 (M+1). $^1$H-NMR (300.13 MHz, CDCl$_3$): δ 1.37 (t, 3H). 3.79 (s, 3H), 3.74-3.82 (br, 2H), 3.83-3.90 (br, 2H), 4.15 (q, 2H), 4.27-4.39 (br, 2H), 5.58 (s, 2H), 6.71 (d, 1H), 7.04 (s, 1H), 7.19 (t, 1H), 7.45-7.50 (m, 1H), 7.64-7.70 (m, 2H), 8.60 (d, 1H).

The following compounds are prepared essentially by the method of Example 23.

| Example No. | Chemical name | Structure | Physical data |
|---|---|---|---|
| 24 | Ethyl 4-[1-ethyl-6-(pyridin-2-ylmethoxy)-1H-pyrrolo[2,3-b]pyridin-3-yl]-3-oxopiperazine-1-carboxylate | 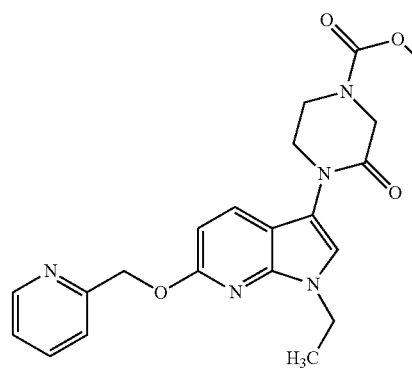 | MS (m/z): 424 (M + 1). |

| Example No. | Chemical name | Structure | Physical data |
|---|---|---|---|
| 25 | Propyl 4-[1-ethyl-6-(pyridin-2-ylmethoxy)-1H-pyrrolo[2,3-b]pyridin-3-yl]-3-oxopiperazine-1-carboxylate | 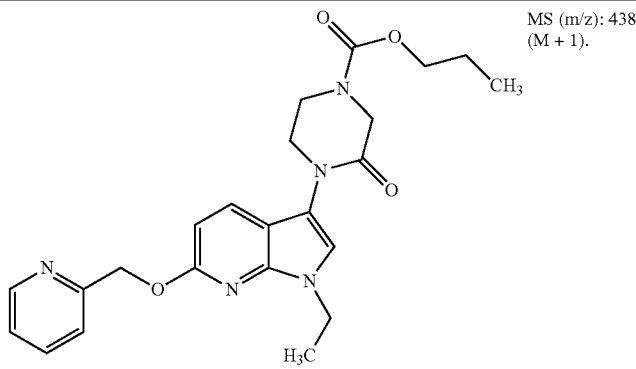 | MS (m/z): 438 (M + 1). |

Example 26

Synthesis of ethyl 4-[5-fluoro-1-methyl-6-(pyridin-2-ylmethoxy)-1H-pyrrolo[2,3-b]pyridin-3-yl]-3-oxopiperazine-1-carboxylate

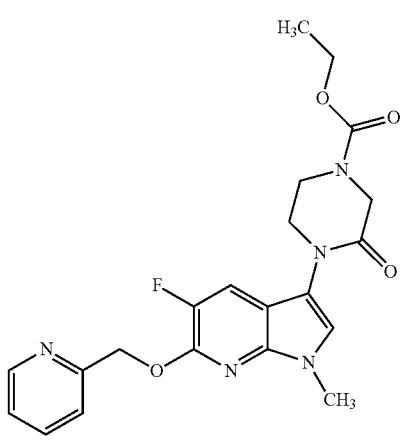 [SMILES: CCOC(=O)N1CCN(c2cn(C)c3nc(OCc4ccccn4)c(F)cc23)C(=O)C1]

3-Bromo-5-fluoro-1-methyl-6-(pyridin-2-ylmethoxy)-1H-pyrrolo[2,3-b]pyridine (0.233 g, 0.693 mmol), 3-oxopiperazine-1-carboxylic acid ethyl ester (0.131 g, 0.762 mmol), N,N'-dimethylethane-1,2-diamine (0.031 mL, 0.284 mmol), copper(I) iodide (0.029 g, 0.152 mmol), potassium phosphate (tribasic, n-hydrate) (0.162 g, 0.762 mmol), and 1,4-dioxane (15 mL) are added together under a nitrogen atmosphere, and heated to reflux overnight with stirring. Further copper (I) iodide (0.120 g, 0.630 mmol) and N,N'-dimethylethane-1,2-diamine (0.120 mL, 1.099 mmol) are then added and the reaction kept at 105° C. for a further 5 h. The reaction is cooled, poured onto brine (ca. 50 mL) and the product extracted with $CHCl_3$ (ca. 3×30 mL). The combined organic extracts are diluted with MeOH, and poured on to a SCX2 ion-exchange column. This is flushed with one column volume of MeOH, and then the product collected in the subsequent one column volume flush of 7 M methanolic ammonia. The solution is then concentrated in vacuo to give a brown oil. This is purified by supercritical fluid chromatography (RT=4.7 minutes (UV); SFC Column. Benzenesulphonamide 21.2 mm×500 mm 5 µm; $CO_2$ Gradient: 15-30% MeOH w/0.2% DMEA in 5.5 mins and then ramped up to 50% MeOH and held for 3.5 mins; Column Temp: 40° C.; Flow Rate: 50.0 ml/min) to give an orange solid. This is then further purified by HPLC chromatography (RT=4.67 minutes (UV); LC Column. Waters Xbridge C18 100 mm×30 mm 5 µm; $H_2O$ w/0.2% $NH_4HCO_3$ Gradient: 9-100% ACN w/0.2% $NH_4HCO_3$ in 6.0 min then held at 100% for 3.0 min; Column Temp: 50° C.; Flow Rate: 3.0 ml/min) to give the title compound as a white solid (0.0621 g, 0.145 mmol). MS (m/z): 428 (M+1). $^1$H-NMR (300.13 MHz, $CDCl_3$): δ 1.32 (t, 3H), 3.72 (s, 3H), 3.73-3.80 (br, 2H), 3.84-3.89 (br, 2H), 4.22 (q, 2H), 4.34 (br, 2H), 5.66 (s, 2H), 7.03 (s, 1H), 7.21 (t, 1H), 7.49 (d, 1H), 7.51-7.55 (m, 1H), 7.70 (td, 1H), 8.60 (d, 1H).

The following compounds are prepared essentially by the method of Example 26.

| Example No. | Chemical name | Structure | Physical data |
|---|---|---|---|
| 27 | Ethyl 4-[5-chloro-1-methyl-6-(pyridin-2-ylmethoxy)-1H-pyrrolo[2,3-b]pyridin-3-yl]-3-oxopiperazine-1-carboxylate | 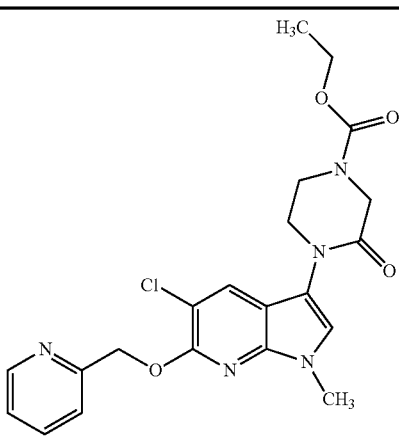 | MS (m/z): 444/446 (M + 1). |
| 28 | Ethyl 4-[1,5-dimethyl-6-(pyridin-2-ylmethoxy)-1H-pyrrolo[2,3-b]pyridin-3-yl]-3-oxopiperazine-1-carboxylate | 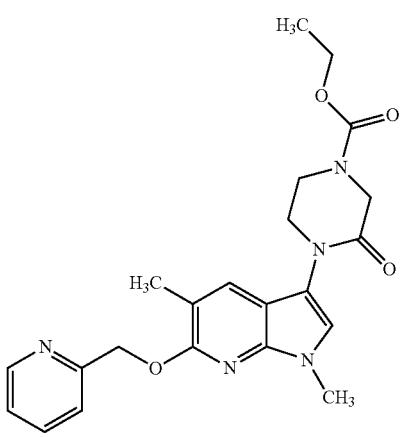 [SMILES: CCOC(=O)N1CCN(c2cn(C)c3nc(OCc4ccccn4)c(C)cc23)C(=O)C1] | MS (m/z): 424 (M + 1). |

We claim:

1. A compound of the formula, or a pharmaceutically acceptable salt thereof,

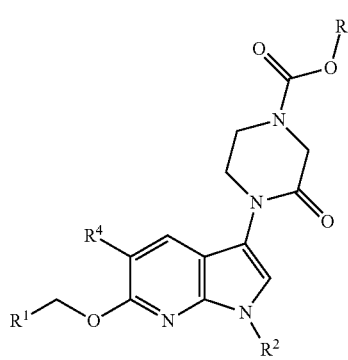

wherein
R$^1$ is pyridinyl optionally substituted with one group selected from fluoro, methyl or methoxy;
R$^2$ is C$_1$-C$_3$ alkyl or cyclopropyl;
R$^3$ is C$_1$-C$_3$ alkyl, 2-fluoroethyl, 2-methoxyethyl, or cyclobutyl; and
R$^4$ is hydrogen, fluoro, chloro or methyl.

2. The compound of claim 1, or a pharmaceutically acceptable salt thereof, wherein R$^1$ is 2-pyridinyl, 3-pyridinyl, 4-pyridinyl, 5-fluoro-2-pyridinyl, 5-methyl-2-pyridinyl, 5-methoxy-2-pyridinyl, 3-methyl-2-pyridinyl or 6-methyl-2-pyridinyl; R$^2$ is methyl, ethyl or cyclopropyl;
R$^3$ is methyl, ethyl, n-propyl, i-propyl, 2-fluoroethyl, 2-methoxyethyl, or cyclobutyl; and
R$^4$ is hydrogen, fluoro, chloro or methyl.

3. The compound of claim 1, or a pharmaceutically acceptable salt thereof, wherein R$^1$ is 2-pyridinyl.

4. The compound of claim 3, or a pharmaceutically acceptable salt thereof, wherein R$^2$ is methyl.

5. The compound of claim 4, or a pharmaceutically acceptable salt thereof, wherein R$^3$ is ethyl.

6. The compound of claim 5, or a pharmaceutically acceptable salt thereof, wherein R$^4$ is hydrogen.

7. The compound of claim 1 which is ethyl 4-[1-methyl-6-(pyridin-2-ylmethoxy)-1H-pyrrolo[2,3-b]pyridin-3-yl]-3-oxopiperazine-1-carboxylate or a pharmaceutically acceptable salt thereof.

8. A pharmaceutical composition comprising a compound of claim 7, or a pharmaceutically acceptable salt thereof, and a pharmaceutically acceptable carrier, diluent or excipient.

9. A method of treating Parkinson's disease comprising administrating to a patient in need thereof an effective amount of a compound of claim 1, or a pharmaceutically acceptable salt thereof.

* * * * *

UNITED STATES PATENT AND TRADEMARK OFFICE
CERTIFICATE OF CORRECTION

| | | Page 1 of 1 |
|---|---|---|
| PATENT NO. | : 8,778,946 B2 | |
| APPLICATION NO. | : 13/882765 | |
| DATED | : July 15, 2014 | |
| INVENTOR(S) | : Carlos Lamas-Peteira et al. | |

It is certified that error appears in the above-identified patent and that said Letters Patent is hereby corrected as shown below:

On the Title Page, Column 2 (Abstract), Line 5, Delete "Parkinsons" and insert -- Parkinson's --, therefor.

In The Claims

Column 48, Line 60 (Approx.), In Claim 8, delete "claim 7," and insert -- claim 1, --, therefor.

Signed and Sealed this
Ninth Day of December, 2014

Michelle K. Lee
*Deputy Director of the United States Patent and Trademark Office*